(12) United States Patent
Hemphill et al.

(10) Patent No.: US 8,229,702 B2
(45) Date of Patent: Jul. 24, 2012

(54) ROBOTIC ARM FOR MOVING A STENT SUPPORT, AND STENT SUPPORT GRIPPER ASSEMBLY

(75) Inventors: Bryan Russell Hemphill, Waterloo (CA); Andrew James McKay, Kitchener (CA); Sang joon Park, Waterloo (CA); Aaron Meyer Waese, Toronto (CA); Anthony S. Andreacchi, San Jose, CA (US); Yung-Ming Chen, Cupertino, CA (US); Arnoldo M. Currlin, San Diego, CA (US); Antonio Garcia, San Jose, CA (US); Jason Van Sciver, Los Gatos, CA (US)

(73) Assignees: Abbott Cardiovascular Systems Inc., Santa Clara, CA (US); ATS Automation Tooling Systems Inc., Ontario (CA)

(*) Notice: Subject to any disclaimer, the term of this patent is extended or adjusted under 35 U.S.C. 154(b) by 0 days.

(21) Appl. No.: 13/021,686

(22) Filed: Feb. 4, 2011

(65) Prior Publication Data

US 2011/0148130 A1    Jun. 23, 2011

Related U.S. Application Data

(62) Division of application No. 11/764,013, filed on Jun. 15, 2007, now Pat. No. 7,885,788.

(51) Int. Cl.
*G01G 17/00* (2006.01)
*G01G 19/03* (2006.01)

(52) U.S. Cl. ......... 702/173; 118/500; 118/719; 702/175

(58) Field of Classification Search .................. 702/102, 702/127, 173, 175; 118/300, 320, 500, 712, 118/719; 427/2.24, 2.35
See application file for complete search history.

(56) References Cited

U.S. PATENT DOCUMENTS

| | | | |
|---|---|---|---|
| 5,897,911 A | 4/1999 | Loeffler | |
| 6,420,666 B1 | 7/2002 | Baumeler et al. | |
| 6,527,863 B1 * | 3/2003 | Pacetti et al. | 118/500 |
| 6,957,152 B1 | 10/2005 | Esbeck | |
| 7,402,329 B2 | 7/2008 | Pacetti et al. | |
| 7,404,979 B1 | 7/2008 | Pacetti | |
| 7,735,449 B1 | 6/2010 | Harold et al. | |
| 7,776,381 B1 | 8/2010 | Tang et al. | |
| 2004/0194704 A1 * | 10/2004 | Chappa et al. | 118/719 |

(Continued)

FOREIGN PATENT DOCUMENTS

| | | |
|---|---|---|
| DE | 100 32 398 | 2/2001 |
| EP | 1 195 584 | 4/2002 |
| WO | WO 2007/130257 | 11/2007 |

OTHER PUBLICATIONS

U.S. Appl. No. 10/750,312, filed Dec. 30, 2003, Desnoyer et al.

(Continued)

*Primary Examiner* — John H Le
(74) *Attorney, Agent, or Firm* — Squire Sanders (US) LLP

(57) ABSTRACT

An apparatus for weighing a stent includes a buffer for storing a stent support with a stent mounted thereon, a stent mounting and dismounting assembly that mounts and dismounts the stent from the stent support, a robotic arm for moving the stent support with the stent between the buffer and the stent mounting and dismounting assembly, and a scale assembly for weighing the stent. The stent mounting and dismounting assembly moves the stent into the scale assembly after the stent has been dismount from the stent support.

14 Claims, 17 Drawing Sheets

U.S. PATENT DOCUMENTS

| | | |
|---|---|---|
| 2006/0035012 A1 | 2/2006 | Pacetti et al. |
| 2007/0003688 A1 | 1/2007 | Chen et al. |
| 2008/0087474 A1 | 4/2008 | Nufer et al. |
| 2008/0307668 A1 | 12/2008 | Watterodt et al. |
| 2008/0311280 A1 | 12/2008 | Rego et al. |
| 2008/0311281 A1 | 12/2008 | Andreacchi et al. |
| 2008/0312747 A1 | 12/2008 | Cameron et al. |
| 2008/0312869 A1 | 12/2008 | Hemphill et al. |

OTHER PUBLICATIONS

U.S. Appl. No. 10/805,047, filed Mar. 18, 2004, Yip et al.

Invitation to pay additional fees, including communication relating to the results of the partial international search, for PCT/US2008/061806, mailed Aug. 27, 2008, 9 pgs.

International Search Report and the Written Opinion, for PCT/US2008/061806, mailed Dec. 5, 2008, 19 pgs.

* cited by examiner

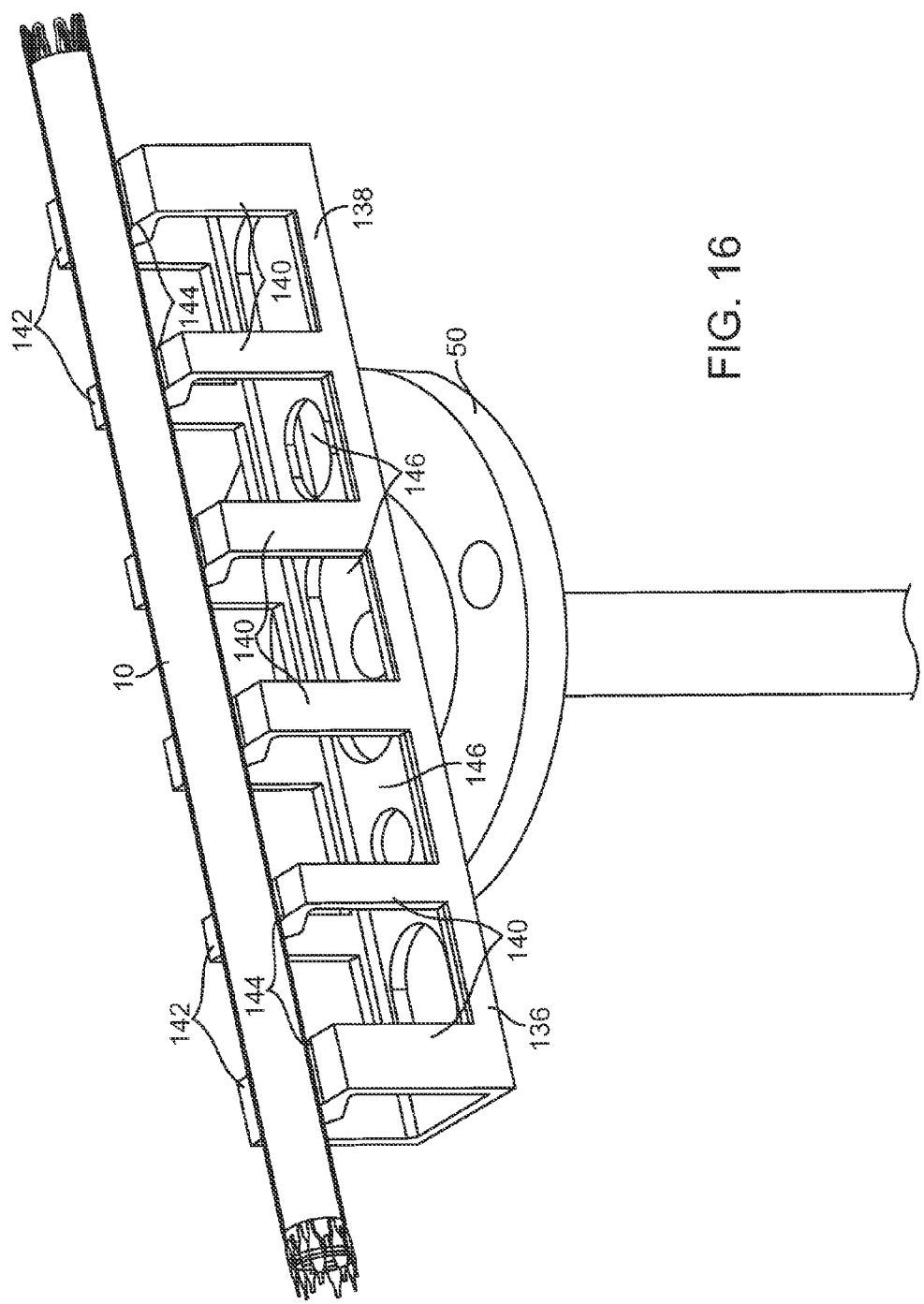

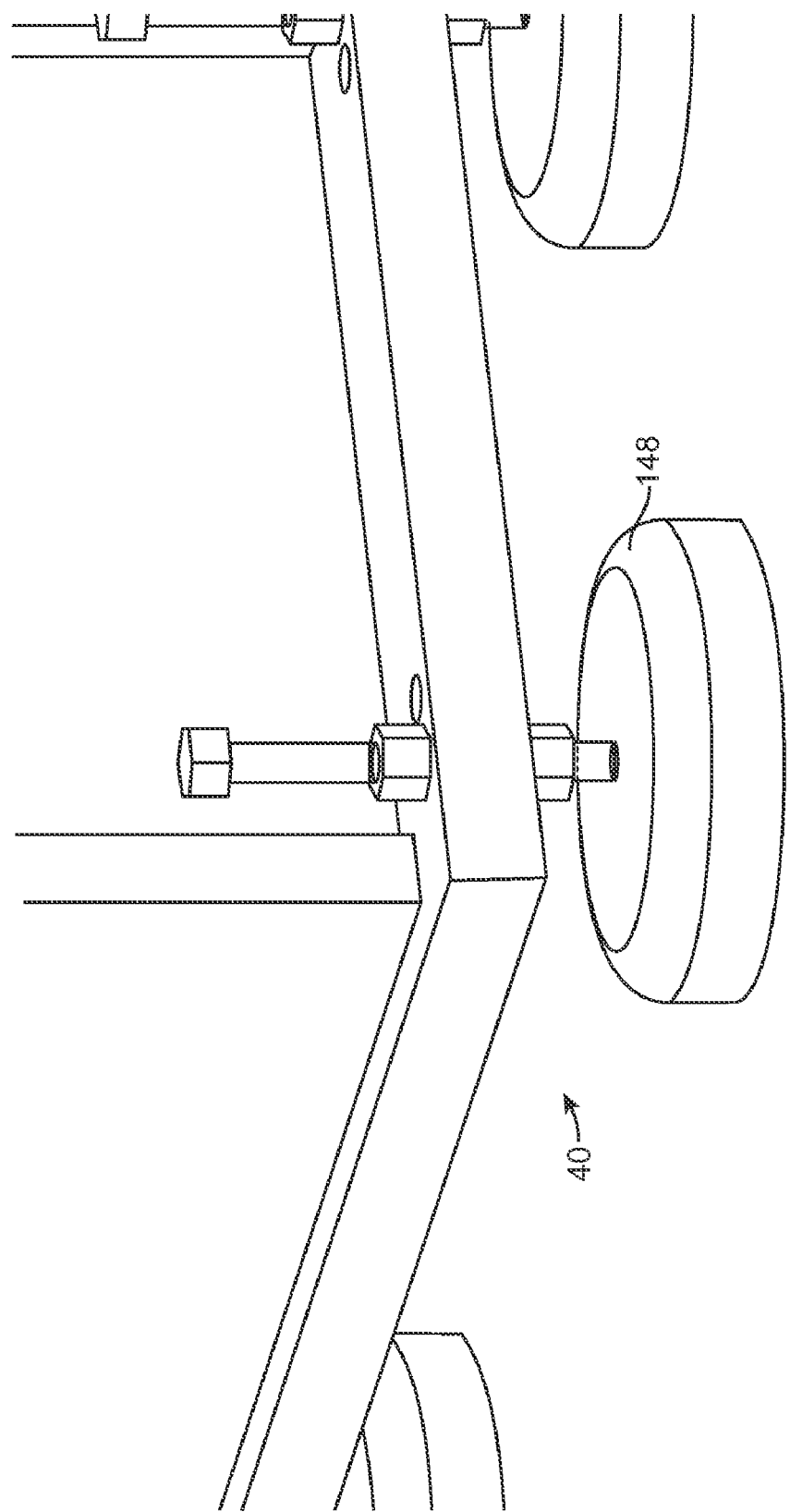

ROBOTIC ARM FOR MOVING A STENT SUPPORT, AND STENT SUPPORT GRIPPER ASSEMBLY

CROSS-REFERENCE TO RELATED APPLICATION

This application is a divisional of application Ser. No. 11/764,013, filed Jun. 15, 2007, now U.S. Pat. No. 7,885,788, which is incorporated herein by reference.

FIELD OF THE INVENTION

This invention relates to a method and apparatus for weighing a stent.

BACKGROUND

Minimally invasive surgical procedures, such as percutaneous transluminal coronary angioplasty (PTCA), have become increasingly common. A PTCA procedure involves the insertion of a catheter into a coronary artery to position an angioplasty balloon at the site of a stenotic lesion that is at least partially blocking the coronary artery. The balloon is then inflated to compress the stenosis and to widen the lumen in order to allow an efficient flow of blood through the coronary artery.

Following PTCA and other stenotic treatment procedures, a significant number of patients experience restenosis or other vascular blockage problems. These problems are prone to arise at the site of the former stenosis.

In order to help avoid restenosis and other similar problems, a stent may be implanted into the vessel at the site of the former stenosis with a stent delivery catheter. A stent is a tubular structure which is delivered to the site of the former stenosis or lesion and compressed against vessel walls thereat, again with a balloon. The structure of the stent promotes maintenance of an open vessel lumen. The stent can be implanted in conjunction with the angioplasty.

Stents can also be used to provide for local delivery of agents. For example, radiotherapy and drug delivery treatments applied to the site of the former stenosis following angioplasty have been found to aid in the healing process and to reduce significantly the risk of restenosis and other similar problems. Local delivery of agents is often preferred over systemic delivery of agents, particularly where high systemic doses are necessary to achieve an effect at a particular site. High systemic doses of agents can often create adverse effects. One proposed method of local delivery is to coat the surface of a stent with an agent.

A stent is typically coated with a primer layer and an agent layer. The primer layer is applied between the stent and the agent layer to improve adhesion of the agent layer to the stent. In some cases, the agent layer may be applied directly to the stent.

Spray coating is commonly used to apply a layer of coating to a stent. A spray coating apparatus typically includes a spray nozzle and a pump that supplies a coating substance from a reservoir to the spray nozzle. The coating substance is ejected through the nozzle to create a plume of coating substance.

During coating operation the stent is supported by a stent support, and the stent support and stent rotate about the axis of the stent support. The stent support is also configured to axially or linearly translate the stent through the plume of coating substance. Alternatively, the nozzle can be translated along the axis of the stent as an alternative to or in addition to axially translating the stent. The coating substance is deposited on the stent as the stent is translated through the plume of the spray nozzle from one end to the other end of the stent. After the spraying operation is stopped, the amount of coating substance on the stent is measured to determine whether it is within a required range. If the amount of stent coating is outside of the range, the stent is considered defective and may be discarded.

The amount of stent coating is typically determined by comparing the weight of an uncoated and coated stent. Currently, the weighing of a stent requires manual manipulation of the stent and stent support. The operator must remove the stent from the stent support and place the stent on a scale to measure stent weight. The operator may need to put the stent support aside if she must manually operate the scale. After a successful measurement of stent weight, the operator picks up the stent support and mounts the stent on the stent support.

This manual procedure has several drawbacks. For example, manual manipulation of the stent may damage the stent or stent coating. For another example, contamination of the stent may result from contact with operator gloves or areas of the weighing station that are not cleaned regularly. Manual loading/unloading of the stent from the delicate scale may damage the scale by overloading or bending the scale post. The damage may cause catastrophic failure of the scale or inaccurate readings. Additionally, the manual procedure is time-consuming. The dismounting of a stent from a stent support and the mounting of a stent on a stent support are delicate tasks, and the operator must be careful to avoid damaging the stent or stent coating. Furthermore, if the operator needs to put the stent support aside to manually operate the scale, she may pick up a wrong stent support and mount the stent thereon. This may have grave consequences because the stent support usually has information identifying the type of stent mounted thereon and the drugs coated on the stent.

Therefore, there is a need for a method and apparatus for efficiently and automatically weighing a stent with minimum risk of damaging the stent or stent coating or mounting the stent on a wrong stent support.

SUMMARY

The present invention is directed to a robotic arm for moving a stent support, and to a stent support gripper assembly.

In aspects of the present invention, a robotic arm for moving a stent support comprises a first member, a second member supporting the first member, a gripper configured to grip a first part of the stent support, and a holder configured to grip a second part of the stent support. The first member is configured to move from a first position to a second position by rotating 180 degrees relative to the second member. The gripper and holder are disposed on a first member, are configured to hold the stent support in a vertical position when the first member is in the first position, and are configured to hold the stent support in a horizontal position when the first member is in the second position.

In aspects of the present invention, a stent support gripper assembly comprises a rail, a first support element gripper for gripping a first support element of a stent support, and a second support element gripper for gripping a second support element of the stent support. The first support element gripper is connected to the rail and configured to move along the rail while gripping the first support element. The second support element gripper is connected to the rail and configured to move along the rail while gripping the second support element. The first support element gripper and the second support element gripper, while both are connected to the rail, are configured to move toward each other along the rail and to move away from each other along the rail.

BRIEF DESCRIPTION OF THE DRAWINGS

FIG. 16 is a perspective view of a stent nest of the scale assembly shown in FIG. 15.

FIG. 17 is a perspective view of a mount of the apparatus shown in FIG. 5.

DETAILED DESCRIPTION OF PREFERRED EMBODIMENTS

A stent used with the present invention may have any structural pattern that is compatible with a bodily lumen in which it is implanted. Typically, a stent is composed of a pattern or network of circumferential and longitudinally extending interconnecting structural elements or struts. In general, the struts are arranged in patterns, which are designed to contact the lumen walls of a vessel and to maintain vascular patency. A myriad of strut patterns are known in the art for achieving particular design goals. A few of the more important design characteristics of stents are radial or hoop strength, expansion ratio or coverage area, and longitudinal flexibility. Embodiments of the present invention are applicable to virtually any stent design and are, therefore, not limited to any particular stent design or pattern. One embodiment of a stent pattern may include cylindrical rings composed of struts. The cylindrical rings may be connected by connecting struts.

In some embodiments, a stent may be formed from a tube by laser cutting the pattern of struts in the tube. The stent may also be formed by laser cutting a metallic or polymeric sheet, rolling the pattern into the shape of the cylindrical stent, and providing a longitudinal weld to form the stent. Other methods of forming stents are well known and include chemically etching a metallic or polymeric sheet and rolling and then welding it to form the stent.

Figure 1:
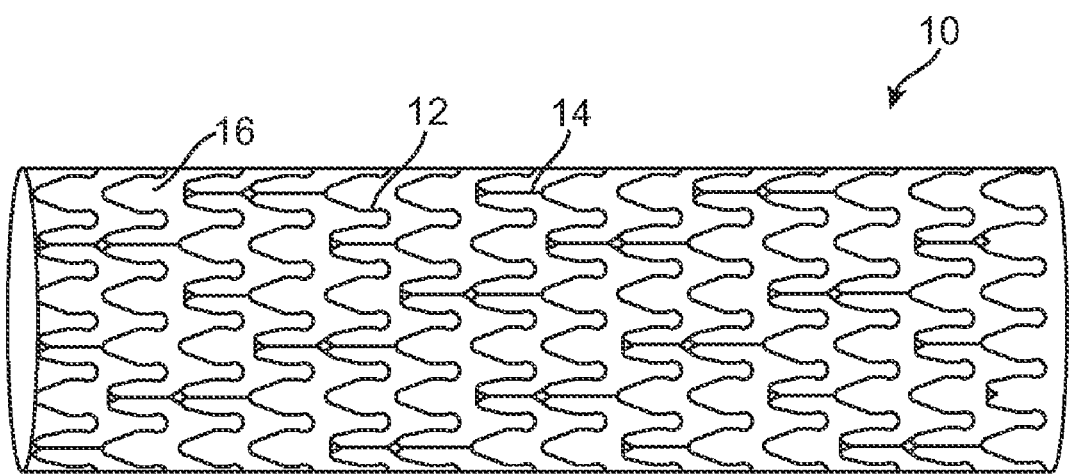
FIG. 1 is a perspective view of a cylindrically-shaped stent.

FIG. 1 illustrates a stent 10 formed from a plurality of struts 12. The plurality of struts 12 are radially expandable and interconnected by connecting elements 14 that are disposed between adjacent struts 12, leaving lateral openings or gaps 16 between adjacent struts 12. The struts 12 and connecting elements 14 define a tubular stent body having an outer, tissue-contacting surface and an inner surface.

The cross-section of the struts 12 in the stent 10 may be rectangular- or circular-shaped. The cross-section of struts is not limited to these, and therefore, other cross-sectional shapes are applicable with embodiments of the present invention. Furthermore, the pattern should not be limited to what has been illustrated as other stent patterns are easily applicable with embodiments of the present invention.

A stent may be coated with any number of layers. For example, the coating of a stent may comprise one or more of the following four types of layers:

(a) an agent layer, which may comprise a polymer and an agent or, alternatively, a polymer free agent;

(b) an optional primer layer including one or more polymers, which layer may improve adhesion of subsequent layers on the implantable substrate or on a previously formed layer;

(c) an optional topcoat layer, which may serve as a way of controlling the rate of release of an agent; and (d) an optional biocompatible finishing layer, which may improve the biocompatibility of the coating.

The agent layer may be applied directly to a stent as a pure agent. Alternatively, the agent can be combined with a biodegradable polymer as a matrix, wherein agent may or may not be bonded to the polymer. The optional primer layer may be applied between the implantable substrate and the agent layer to improve adhesion of the agent layer to the implantable substrate and can optionally comprise an agent. A pure agent layer can be sandwiched between layers comprising biodegradable polymer. The optional topcoat layer may serve as a membrane to control the rate of release of the bioactive agent and can optionally comprise agent. The biocompatible finishing layer may also be applied to increase the biocompatibility of the coating by, for example, increasing acute hemocompatibility and can also comprise an agent.

The polymers in the agent layer and optional primer layer can be biostable, bioabsorbable, biodegradable, or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and eventual absorption and elimination of the polymer can be caused by, for example, hydrolysis, metabolic processes, bulk or surface erosion, and the like.

The therapeutic agent can include any substance capable of exerting a therapeutic or prophylactic effect. Examples of therapeutic agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The bioactive agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, (e.g., TAXOL® by Bristol-Myers Squibb Co., Stamford, Conn.), docetaxel (e.g., Taxotere®, from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include aspirin, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, proteins, peptides, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate agents include cisplatin, insulin sensitizers, receptor tyrosine kinase inhibitors, carboplatin, alpha-interferon, genetically engineered epithelial cells, steroidal anti-inflammatory agents, non-steroidal anti-inflammatory agents, antivirals, anticancer drugs, anticoagulant agents, free radical scavengers, estradiol, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, ABT-578, clobetasol, cytostatic agents, prodrugs thereof, co-drugs thereof, and a combination thereof. Other therapeutic substances or agents may include rapamycin and structural derivatives or functional analogs thereof, such as 40-O-(2-hydroxy)ethyl-rapamycin (everolimus), 40-O-(3-hydroxy) propyl-rapamycin, 40-O-[2-(2-hydroxy)ethoxy]ethyl-rapamycin, and 40-O-tetrazole-rapamycin.

Figure 2:
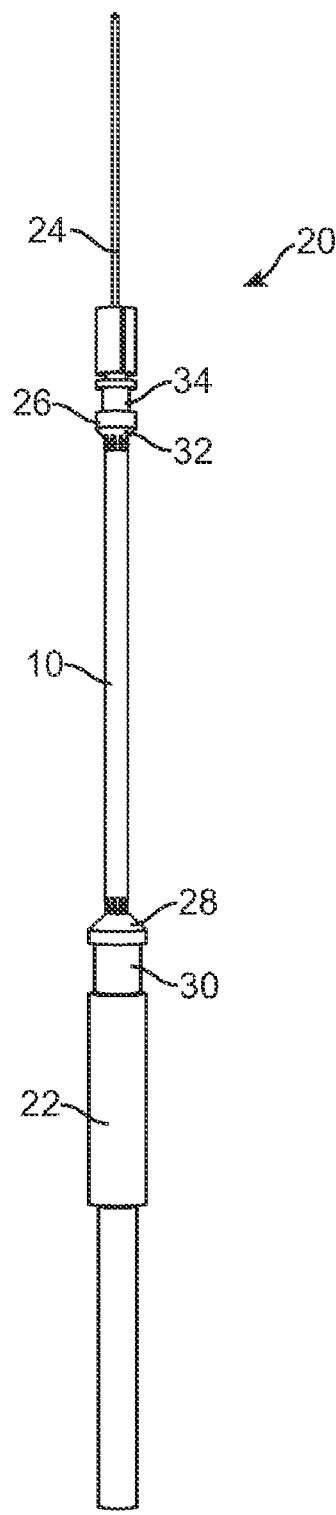
FIG. 2 is a perspective view of a stent support.

Typically, the stent is mounted on a stent support during stent coating operation. Referring to FIG. 2, a stent support 20 may include a first support element 22, a core element 24, and a second support element 26. The first support element of the stent support may be, for example, a shank. The second support element of the stent support may be, for example, a collet. The first support element 22 may be connected to a motor (not shown) to provide rotational motion about the longitudinal axis of the first support element 22 during coating.

The first support element 22 preferably includes a conical portion 28, tapering inwardly at an angle of, for example, about 15° to about 75°, more narrowly from about 30° to about 60°. In some cases, the angle can be about 45°. In the illustrated embodiment, a first end of the core element 24 is permanently affixed to the conical portion 28 of the first support element 22. Alternatively, the first support element may include a bore for receiving an end of the core element, and the end of the core element may be threaded to screw into the bore. The first support element 22 may also include a circumferential groove 30.

The second support element 26 also includes a conical portion 32 having an inwardly tapered angle which can be the same as or different from the tapered angle of the first support element's conical portion 28. The second support element 26 has a through bore. A second end (free end) of the core element 24 can extends into the through bore of the second support element 26 and can be press-fitted or friction-fitted within the bore to prevent the second support element 26 from freely moving on the core element 24. The second support element 26 may also include a circumferential groove 34.

Figure 3:
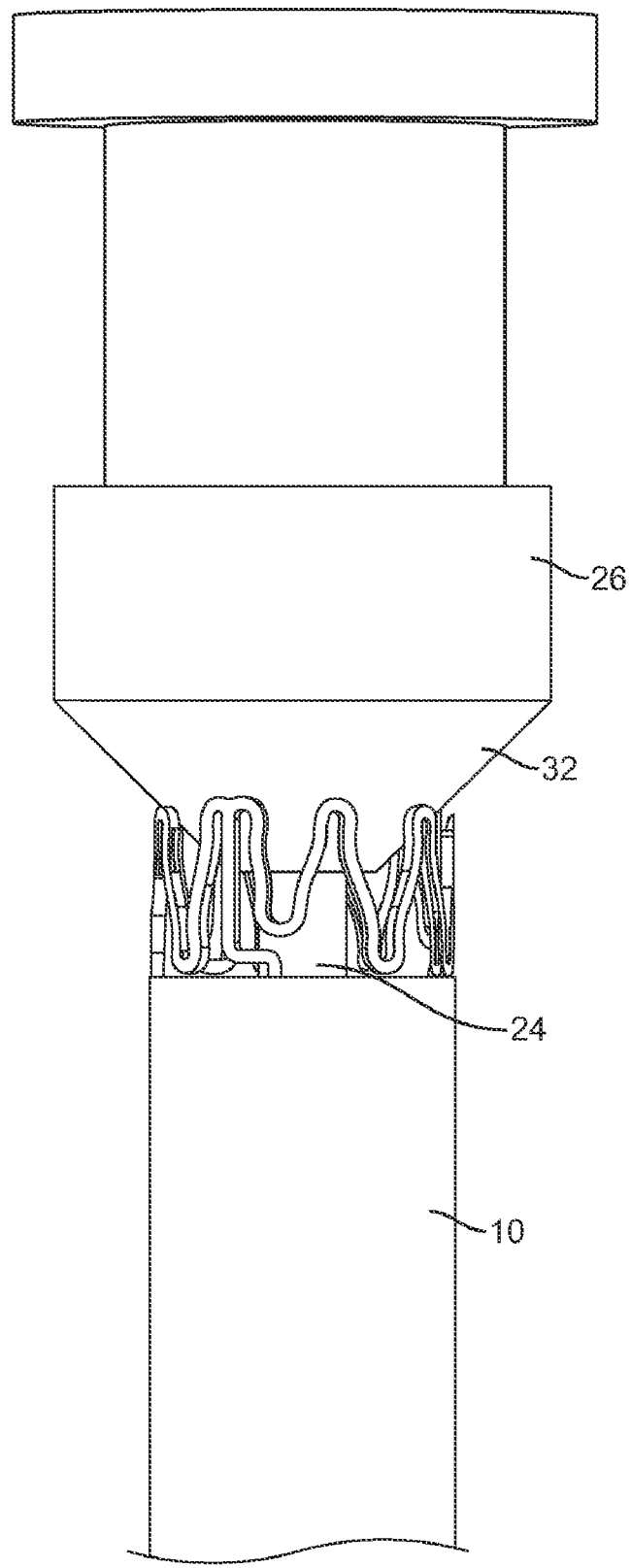
FIGS. 3 and 4 are perspective views showing the conical portions of the first and second support elements of a stent support supporting the ends of a stent.
Figure 4:
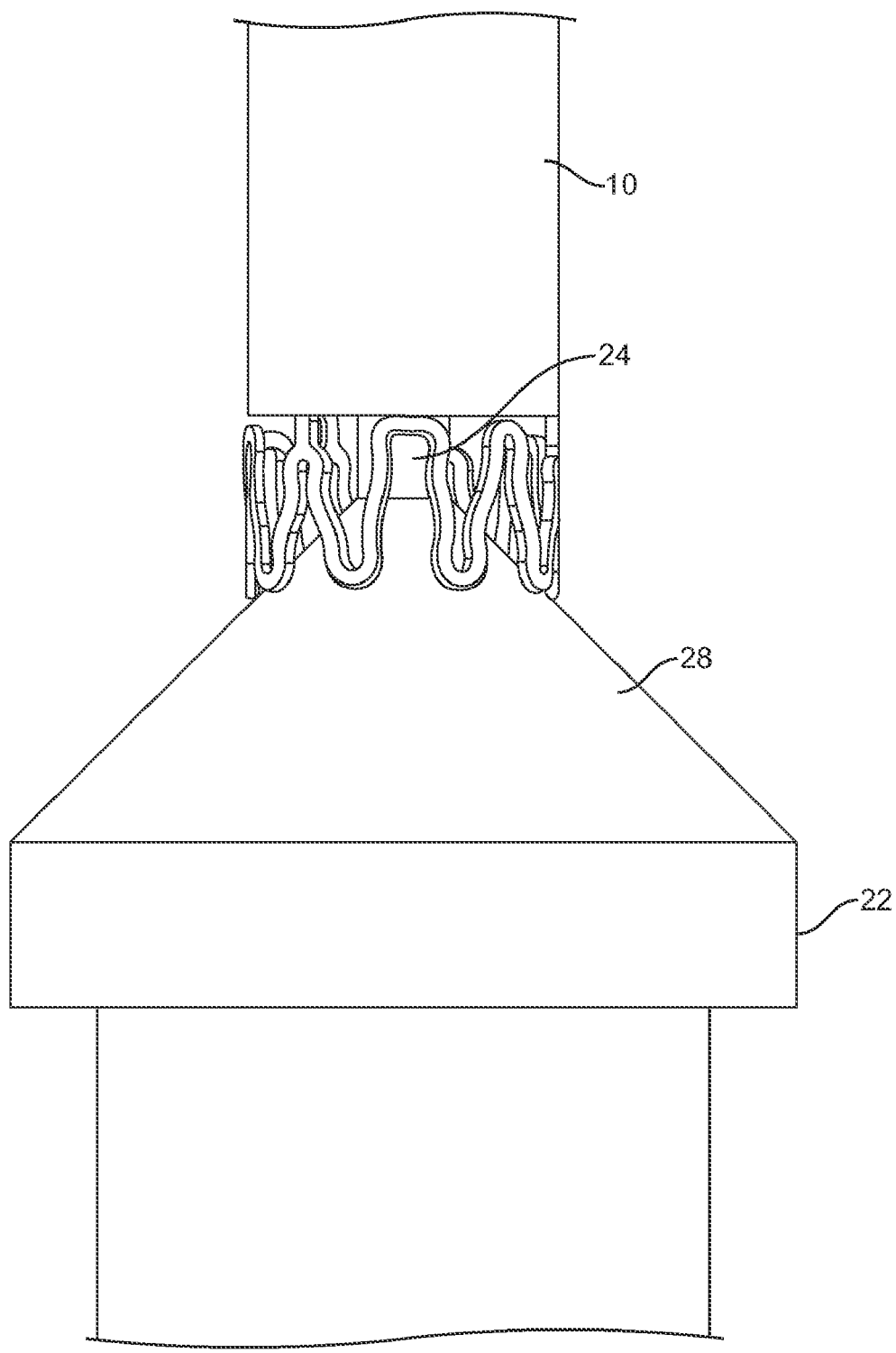

The stent support 20 supports the stent 24 via the conical portions 28, 30 of the first and second support elements 22, 26. FIG. 3 shows that the conical portion 28 of the first support element 22 supports one end of the stent 24, and FIG. 4 shows that the conical portion 32 of the second support element 26 supports the other end of the stent 24. In FIGS. 3 and 4 and in subsequent Figures, only the struts in the end rings of the stent are shown, and the struts in the rest of the stent are not shown. As the conical portions 28, 30 of the first and second support elements 22, 26 are advanced towards each other, they automatically cause the stent 24 to become centered about the core element 24, and they also secure the stent 24 in the longitudinal direction of the stent support 20. The only contact between the stent 24 and the stent support 20 is at the interface between the conical portions 28, 30 and the inner rims at the ends of the stent 24.

Figure 5:
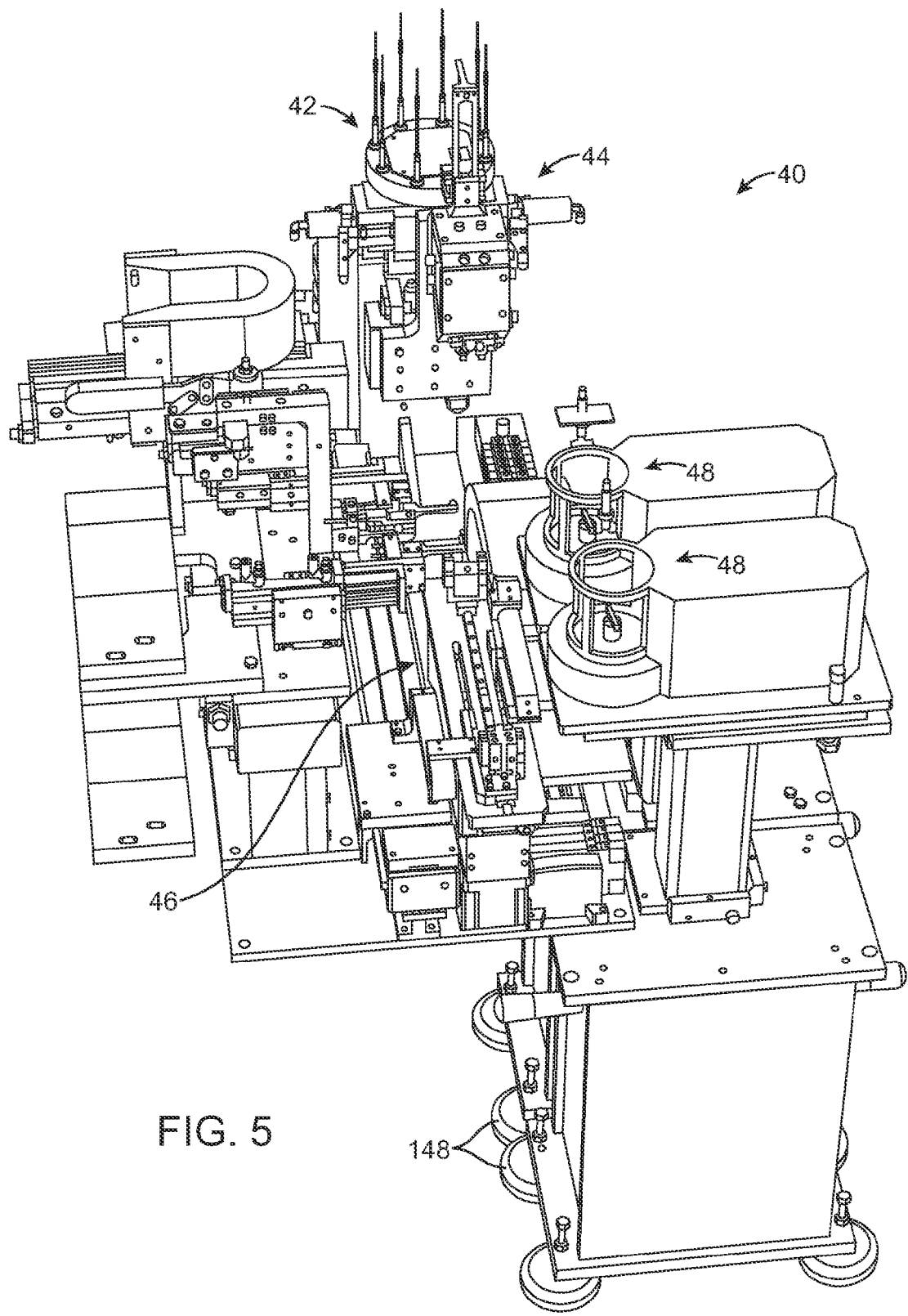
FIG. 5 is a perspective view of an apparatus for weighing a stent according to the present invention.

One aspect of the present invention relates to an apparatus for weighing a stent. FIG. 5 illustrates an example 40 of such an apparatus. The apparatus 40 includes a buffer 42, a robotic arm 44, a stent mounting and dismounting assembly 46, and scale assemblies 48 each of which has a scale 50.

The buffer 42 is used to store stent supports 20 with stents 10 mounted thereon before and after the stents 10 have been weighed on the scales 50. The robotic arm 44 moves a stent support 20 from the buffer 42 to the stent mounting and dismounting assembly 46. The stent mounting and dismounting assembly 46 removes the stent 10 from the stent support 20 and places the stent 10 on a scale 50 to be weighed. After the stent 10 has been weighed, the stent mounting and dismounting assembly 46 removes the stent 10 from the scale 50 and mounts the stent 10 on the stent support 20. The robotic arm 44 moves the stent 10 and stent support 20 from the stent mounting and dismounting assembly 46 to the buffer 42.

The buffer 42 may be used to store stents 20 that are at various stages of the coating process. The weighing of a stent 10 may take place before the stent 10 is coated and after any one of various processes involved the coating of the stent, such as polymer coating, agent coating, drying, etc. These processes are not synchronized with the weighing of the stents. In some situations, several stents 20 to be weighed may be received in a short period of time at the weighing apparatus 40, while in other situations no stents may be received for a relatively long period of time at the weighing apparatus 40. If a buffer is not provided, a stent may have to be held at a coating station (or any other stage of the coating process) before it is weighed. As a result, the coating station lies idle until a scale 50 is available to weigh the stent. Alternatively, the scale 50 may lie idle when no stents are sent to the scale 50 to be weighed.

Figure 6:
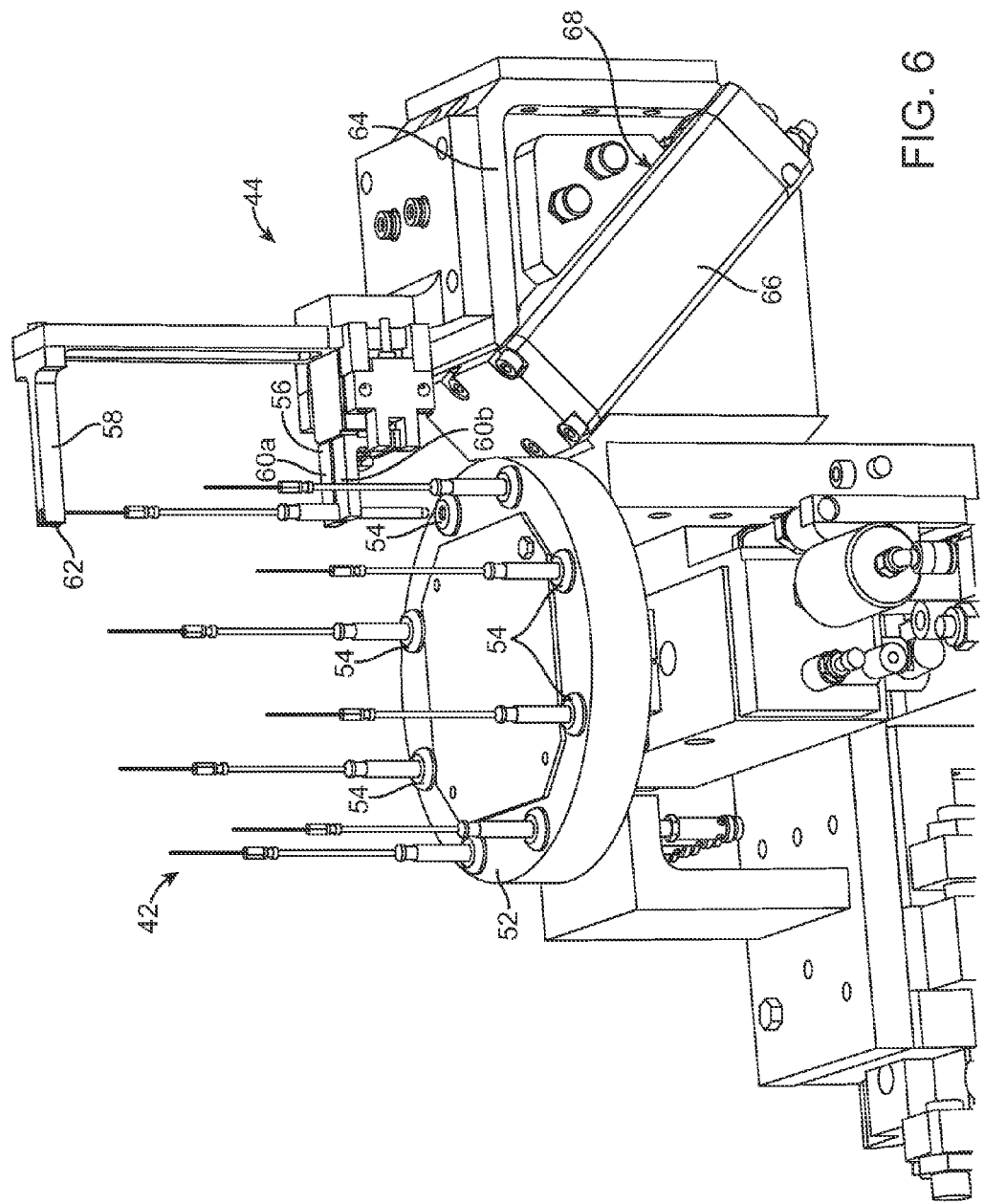
FIG. 6 is a perspective view of a buffer and a robotic arm of the apparatus shown in FIG. 5.

A buffer of the present invention may have any suitable configuration and structure. For example, as shown in FIG. 6, the buffer 42 may have a circular plate 52 and one or more receptacles 54 for receiving stent supports 20 that are arranged in a circle along the edge of the circular plate 52. Each receptacle 54 may hold the first support element 22 of a stent support 20, thereby placing the stent support 20 in a vertical position as shown in FIG. 6. The buffer 42 may include an electric or hydraulic motor (not shown) to rotate the buffer plate 52 and a controller (not shown) that can control the rotation of the buffer plate 52 to align a particular stent support 20 with the robotic arm 44 for pickup.

Alternatively, a buffer of the present invention may be similar to a conveyor belt and may include receptacles spaced at a fixed or variable interval on the convey belt. The movement of the conveyor belt may be controlled to align a particular stent support 20 with the robotic arm 44 for pickup.

A receptacle 54 of the buffer 42 may be designated to receive stents 10 that are at a particular stage of the coating process. As shown in FIG. 6, a receptacle 54 may be used to hold a stent that is clean (i.e., before it is coated) and needs to be weighed. Another receptacle 54 may be used to hold a stent that is clean and has been weighed. A further receptacle 54 may be used to hold a stent that has been baked (i.e., coated and dried in an oven) and has not be weighed. A still further receptacle 54 may be used to hold a stent that has been baked (i.e., coated and dried in an oven) and has been weighed.

The robotic arm 44 may be used to perform various functions. Preferably, the robotic arm 44 is able to grip and hold a stent support 20, to pick up a stent support 20 from and to place it in a receptacle 54 of the buffer 42, to pick up a stent support 20 from and to place it on the stent mounting and dismounting assembly 46, and/or to move a stent support 20 between the buffer 42 and the stent mounting and dismounting assembly 46.

The robotic arm 44 may have any suitable structural features that can be used to grip and hold a stent support 20. In the embodiment shown in FIG. 6, for example, the robotic arm 44 has a stent support griper 56 for gripping the first support element 22 of the stent support 20, and a holder 58 for holding the free end of the core element 24 of the stent support 20 to keep the stent support 20 straight. The stent support griper 56 may have two fingers 60a, 60b that can move away from each other to allow the first support element 22 to be placed between the fingers 60a, 60b and can move towards each other to grip the first support element 22. The core element holder 58 may have a groove 62 at its tip for receiving and holding the core element 24 of the stent support 20.

The robotic arm 44 may be moveable between two positions. The first position of the robotic arm 44 is shown in FIG. 6 where the robotic arm 44 is positioned next to the buffer 42 and can hold the stent support 20 in a vertical position. At the second position the robotic arm 44 is positioned next to the stent mounting and dismounting assembly 46 and holds the stent support 20 in a horizontal position. When the robotic arm 44 moves from the first position to the second position, it moves a stent support 20 from the buffer 42 to the stent mounting and dismounting assembly 46. When the robotic arm 44 moves from the second position to the first position, it moves a stent support 20 from the stent mounting and dismounting assembly 46 to the buffer 42.

To enable the robotic arm's movement between its first and second positions, the robotic arm 44 has first and second members 64, 66, each of which has a generally triangular configuration when viewed as shown in FIG. 6. The interface 68 between the two members 64, 66 is at a 45° from either the vertical or horizontal position. The first member 64 can rotate relative to the second member 66 at the interface 68. In other words, the first member 64 can rotate about an axis that is perpendicular to the interface 68. When the first member 64 is rotated 180° from the first position shown in FIG. 6, the stent support 20 is moved from the vertical position at the buffer 42 to a horizontal position just above the stent mounting and dismounting assembly 46. When the first member 64 is rotated back to the first position as shown in FIG. 6, the stent support 20 is moved from the horizontal position back to the vertical position shown in FIG. 6.

Additionally, the entire robotic arm 44 may move vertically between a first, lower position and a second, higher position shown in FIG. 6.

To move a stent support 20 from the buffer 42 to the stent mounting and dismounting assembly 46, the robotic arm 44 is first placed in its first position next to the buffer 42 and at the lower vertical position. The robotic arm 44 then grips the stent support 20 with its stent support griper 56 gripping the first support element 22 of the stent support 20 and the core element holder 58 holding the core element 24 of the stent support 20. At this point, the stent support 20 is still placed in a receptacle 54 of the buffer 42. Then the robotic arm 44 is raised to the higher vertical position, as shown in FIG. 6, to lift the stent support 20 out of the receptacle 54. The first member 64 of the robotic arm 44 is then rotated 180° relative to the second member 66 to move the stent support 20 from the vertical position shown in FIG. 6 to a horizontal position just above the stent mounting and dismounting assembly 46. Next the robotic arm 44 is lowered from its higher vertical position to its lower vertical position to place the stent support 20 on the stent mounting and dismounting assembly 46.

The stent mounting and dismounting assembly 46 is used to mount a stent 10 on a stent support 20 or dismount a stent 10 from a stent support 20. To that end, the assembly 46 may be equipped with a stent support gripper assembly 70 and a stent gripper assembly 72. The stent support gripper assembly 70 is used to hold a stent support 20 when a stent 10 is being mounted on or dismounted from the stent support 20. The stent gripper assembly 72 is used to holder the stent 10 when the stent 10 is being mounted on or dismounted from a stent support 20.

Figure 7:
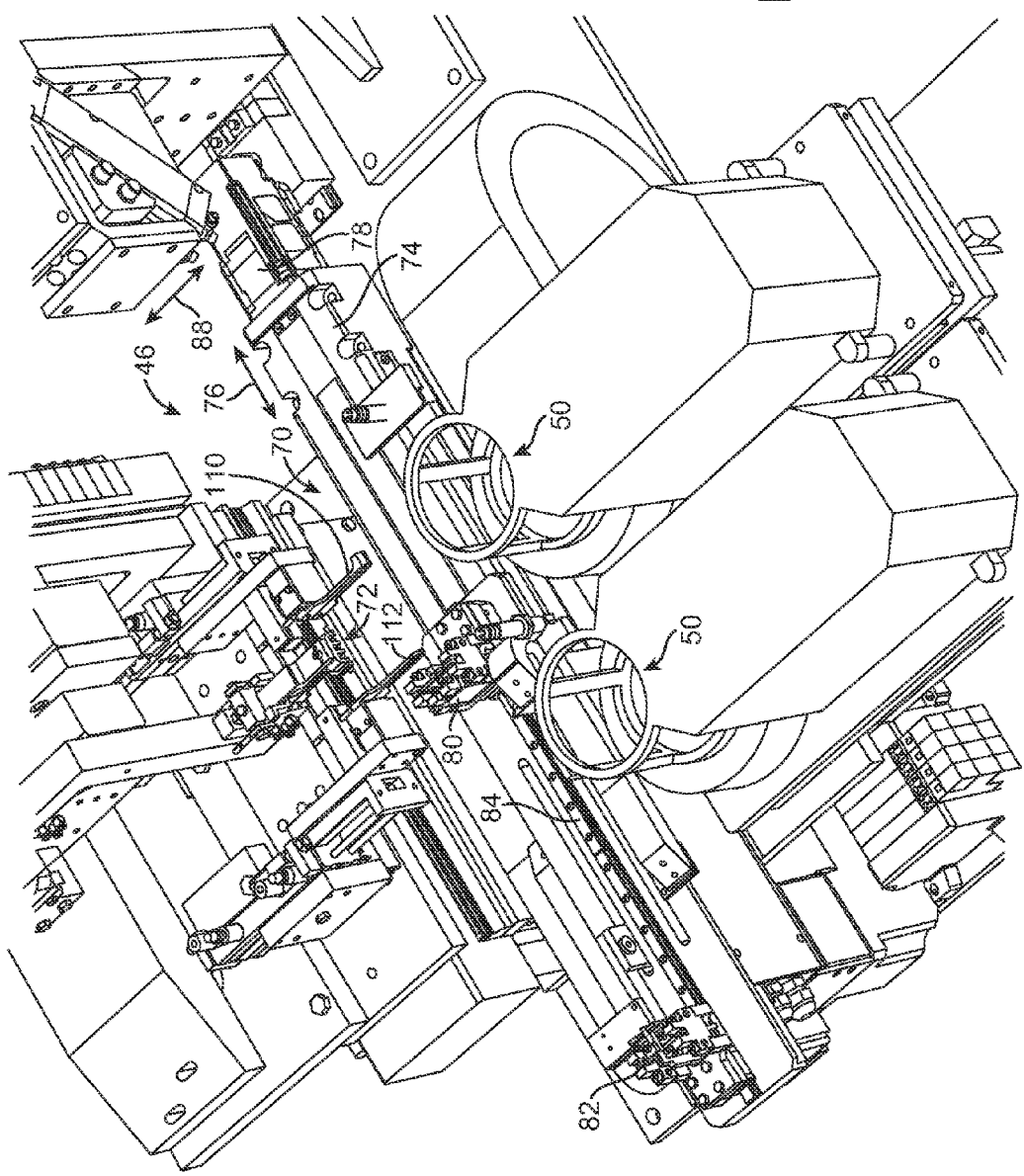
FIG. 7 is a perspective view of a stent mounting and dismounting assembly of the apparatus shown in FIG. 5, wherein the stent mounting and dismounting assembly includes a stent support gripper assembly, a stent gripper assembly, and first and second core element guides.

As shown in FIG. 7, the stent support gripper assembly 70 may include a platform 74 that is moveable in a longitudinal direction 76 along a longitudinal rail 78. The stent support gripper assembly 70 may further include a first support element gripper 80 and a second support element gripper 82. The first and second support element grippers 80, 82 are mounted on the platform 74 and are moveable independently of each other in the longitudinal direction 76 along a longitudinal platform rail 84 on the platform 74. In other words, the first and second support element grippers 80, 82 can move in the longitudinal direction 76 as part of the platform 74, or they can move in the longitudinal direction 76 relative to the platform 74. Alternatively, the stent support gripper assembly 70 may not include the platform 74. Instead the first and second support element grippers 80, 82 may be mounted directly on the rail 78 for longitudinal movement.

Figure 8:
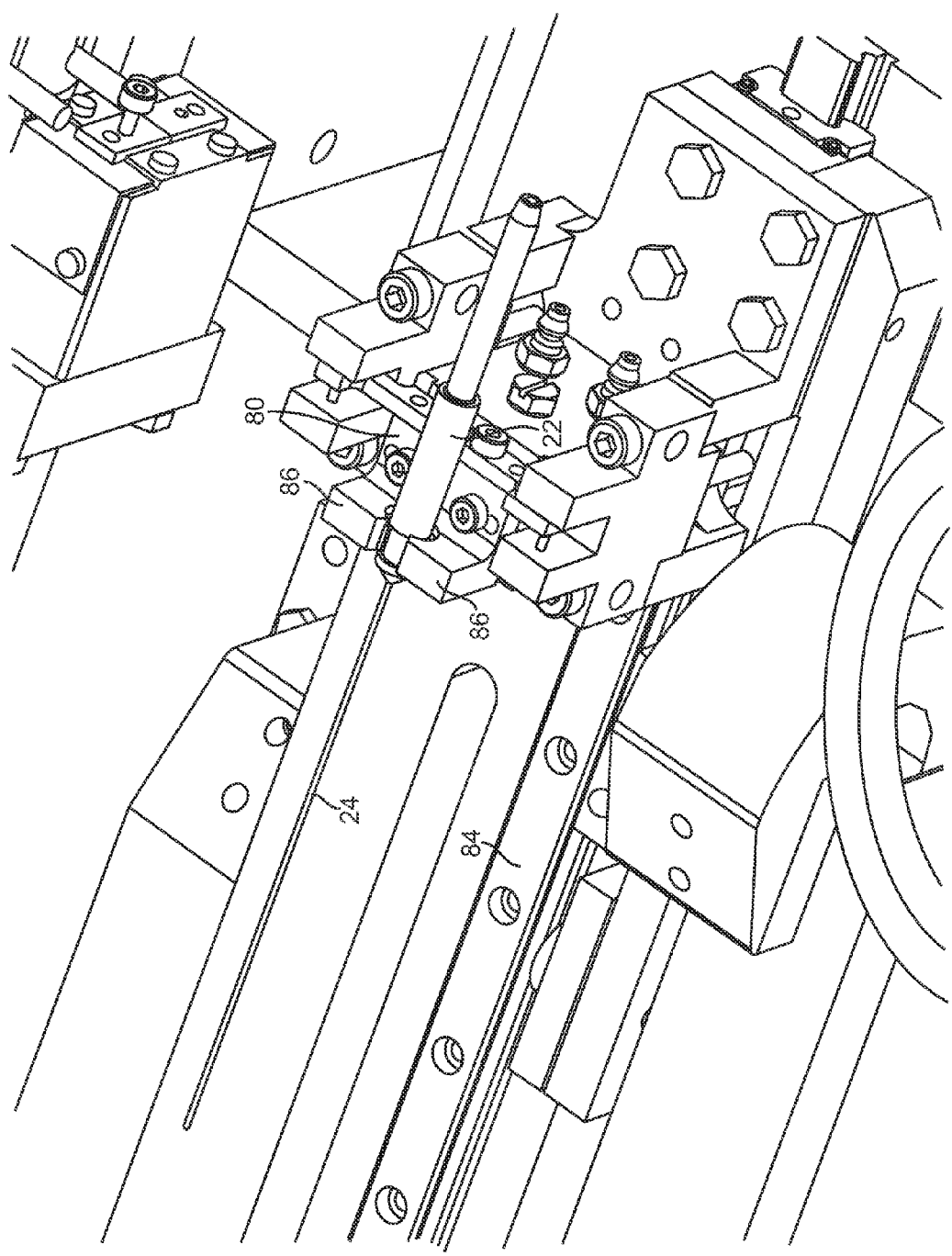
FIG. 8 is a perspective view of a first support element gripper of the stent support gripper assembly shown in FIG. 7, wherein a first support element is held in the first support element gripper.
Figure 9:
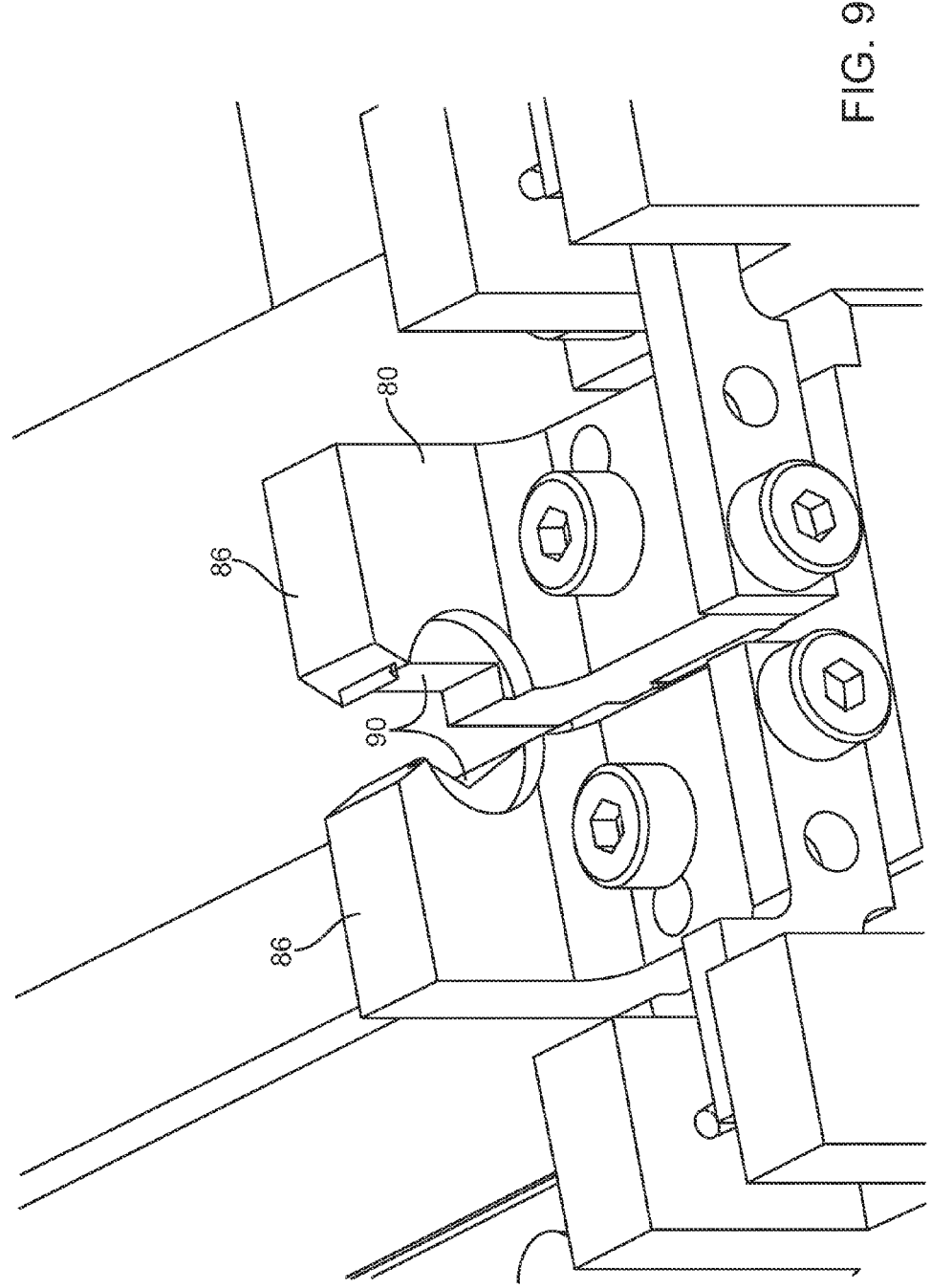
FIG. 9 is another perspective view of the first support element gripper shown in FIG. 8, wherein a first support element is not held in the first support element gripper.

As shown in FIG. 8, the first support element gripper 80 is used to grip and hold the first support element 22 of the stent support 20. The first support element gripper 80 may include two fingers 86 that extend upwards and can move in the lateral direction 88. The two fingers 86 can move away from each other so that the first support element 22 can be placed between the two fingers 86. And the two fingers 86 can move towards each other to grip the first support element 22. The two fingers 86 may grip the first support element 22 at its groove 30. In other words, when the two fingers 86 grip the first support element 22, they are placed within the groove 30 of the first support element 22. Preferably, the longitudinal dimension of the fingers 86 is substantially the same or slightly less than the width of the groove 30 so that the fingers 86, when placed in the groove 30, may limit the longitudinal movement of the first support element 22. Additionally, each of the fingers 86 may include a groove (or cut) 90 for receiving the first support element 22 (or the groove 30 of the first support element 22). The grooves 90 of the fingers 86 help ensure that the first support element 22 is securely held between the fingers 86. One or both of the grooves 90 may have a substantially semi-circular configuration, and the radius of the semi-circle may be substantially the same or slightly larger than the diameter of the first support element 22 (or the diameter of the groove 30 of the first support element 22). Alternatively, one or both of the grooves 90 may have a substantially triangular configuration. In the embodiment shown in FIG. 8, one of the grooves 90 has a triangular configuration (see FIG. 9) while the other groove 90 has a rectangular configuration.

Figure 10:
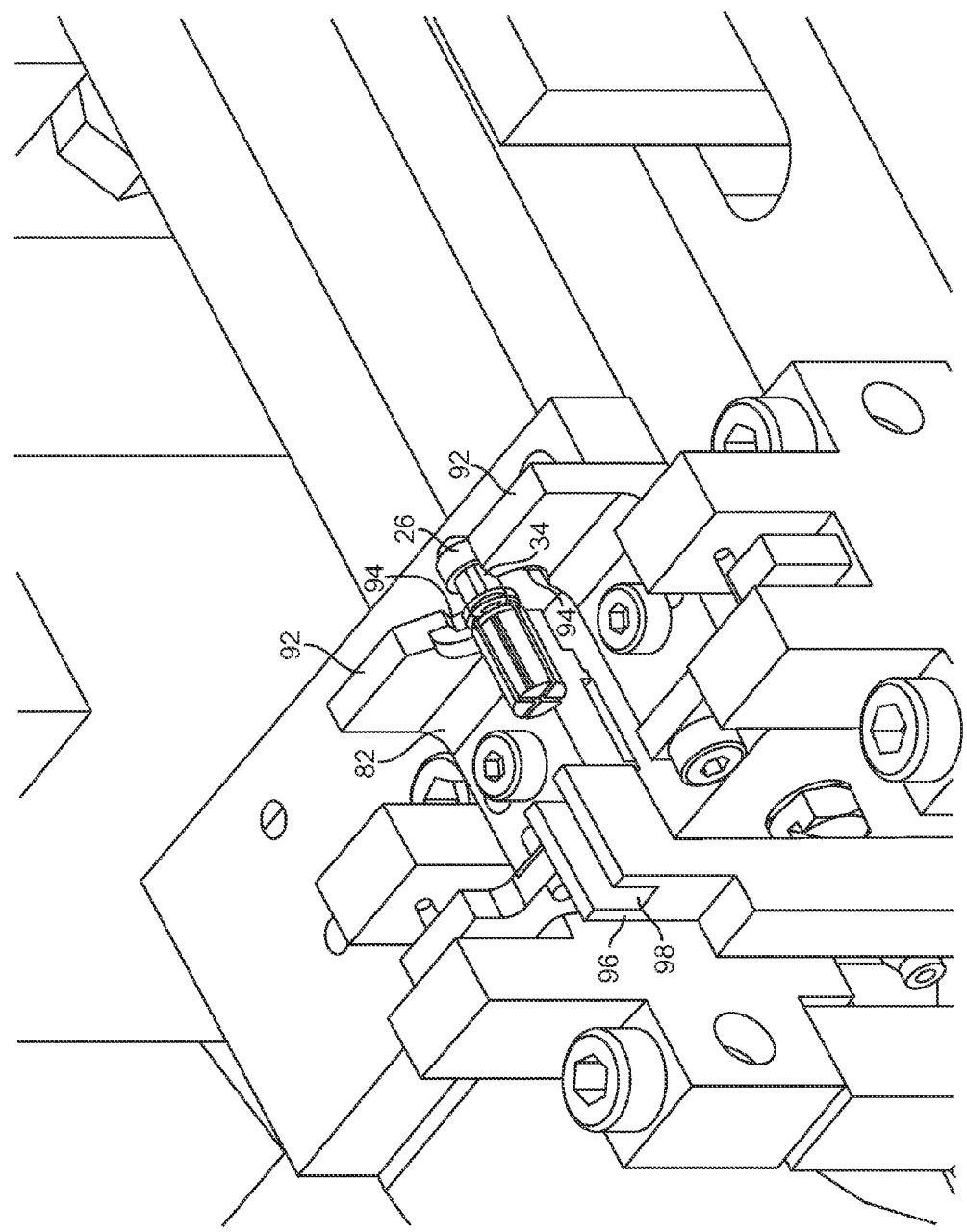
FIG. 10 is a perspective view of a second support element gripper of the stent support gripper assembly shown in FIG. 7, wherein a second support element is held in the second support element gripper.

As shown in FIG. 10, the second support element gripper 82 is used to grip and hold the second support element 26 of the stent support 20. The second support element gripper 82 may also include two fingers 92 that extend upwards and can move in the lateral direction 88. The two fingers 92 can move away from each other so that the second support element 26 can be placed between the two fingers 92. And the two fingers 92 can move towards each other to grip the second support element 26. Preferably, the two fingers 92 grip the second support element 26 at its groove 34. Preferably, the longitudinal dimension of the fingers 92 is substantially the same or slightly less than the width of the groove 34 so that the fingers 92, when placed in the groove 34, may limit the longitudinal movement of the second support element 26. Additionally, each of the fingers 92 may include a groove 94 for receiving the second support element 26 (or the groove 34 of the first support element 26). The grooves 94 of the fingers 92 help ensure that the second support element 26 is securely held between the fingers 92. One or both of the grooves 94 may have a substantially semi-circular configuration, and the radius of the semi-circle may be substantially the same or slightly larger than the diameter of the second support element 26 (or the diameter of the groove 34 of the second support element 26). Alternatively, one or both of the grooves 94 may have a substantially triangular configuration. In the embodiment shown in FIG. 10, one of the grooves 94 has a triangular configuration while the other groove 94 has a rectangular configuration.

Preferably, the second support element gripper 82 includes also a core element holder 96 for holding the free end of the core element 24 of the stent support 20. The core element holder 96 has a groove 98 for receiving and holding the free end of the core element 24.

During the dismounting of a stent 10 from a stent support 20, the stent gripper assembly 72 grips and holds the stent 10, and the first and second support element grippers 80, 82 grip and hold the first and second support elements 22, 26 of the stent support 20, respectively. At this point, the first and second support element grippers 80, 82 may move away from each other in the longitudinal direction 76 along the platform rail 84. This movement removes the second support element 26 of the stent support 20 from the core element 24 of the stent support 20. The movement of the first support element gripper 80 also extracts the core element 24 of the stent support 20 from the hollow center of the stent 10. As a result, the stent 10 is removed from the stent support 20.

During the mounting of a stent 10 on a stent support 20, the stent gripper assembly 72 places the stent 10 in a position where the stent 10 is substantially coaxial with the first and second support elements 22, 26 and core element 24 of the stent support 20 and where the stent is between the first and second support elements 22, 26. The first and second support element grippers 80, 82 move the first and second support elements 22, 26 of the stent support 20 towards each other in the longitudinal direction 76. This movement threads the core element 24 of the stent support 20 through the hollow center of the stent 10. The movement also mounts the second support element 26 on the core element 24 of the stent support 20. As a result, the stent 10 is mounted on the stent support 20.

Figure 11:
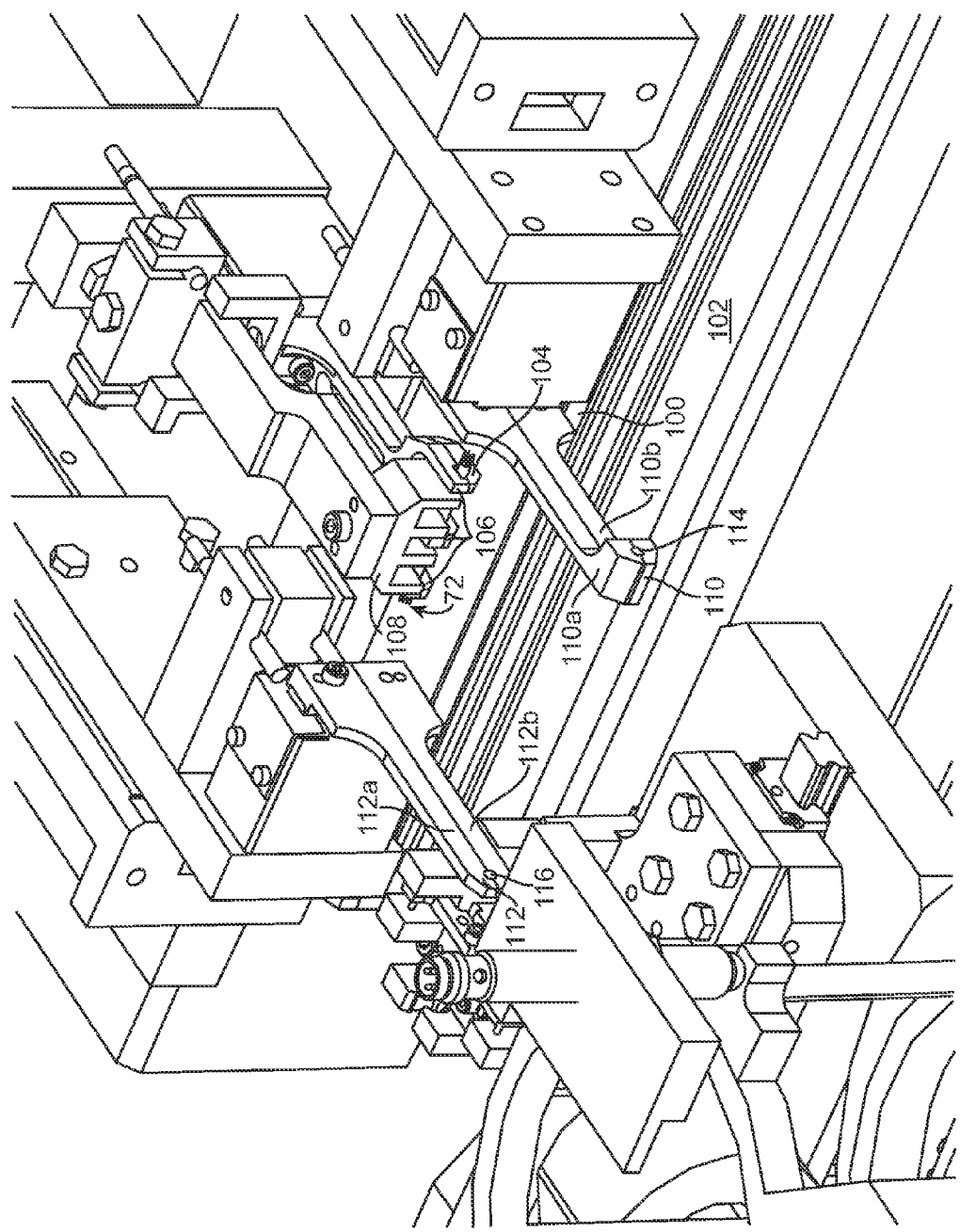
FIG. 11 is a detailed perspective view of the stent gripper assembly and first and second core element guides shown in FIG. 7.

As shown in FIG. 11, the stent gripper assembly 72 preferably includes a platform 100 that is moveable in a longitudinal direction 76 along a longitudinal rail 102. This longitudinal rail 102 is arranged side by side and in parallel with the longitudinal rail 78 on which the stent support gripper assembly 70 is moveably placed.

The stent gripper assembly 72 may include a stent gripper 104 that is mounted on and moveable with the platform 100 of the stent gripper assembly 72. Alternatively, the stent gripper assembly 72 may not include the platform 100. Instead the stent gripper 104 may be directly mounted on the rail 102 for longitudinal movement.

The stent gripper 104 may also be moveable in the lateral direction 88 and may have at least three lateral positions. The first lateral position (i.e., a middle position) is described above where the stent gripper 104 grips and holds the stent 10 when the stent 10 is being mounted on or dismounted from the stent support 20. At this position, as described above, the stent 10 is substantially coaxial with the first and second support elements 22, 26 and core element 24 of the stent support 20. The second lateral position of the stent gripper 104 is a retracted position, as shown in FIG. 11, where the stent gripper 104 is retracted from the first lateral position. The stent gripper 104 moves to the retracted position after the stent gripper 104 releases the stent 10 subsequent to a successful mounting of the stent 10 on the stent support 20. A retracted stent gripper 104 allows the robotic arm 44 to move the stent 10 from the second support element gripper 82 to the buffer 42. The third lateral position of the stent gripper 104 is an extended position where the stent gripper 104 extends into one of the scale assemblies 48 to place the stent 10 on or to remove the stent 10 from the scale 50.

Figure 12:
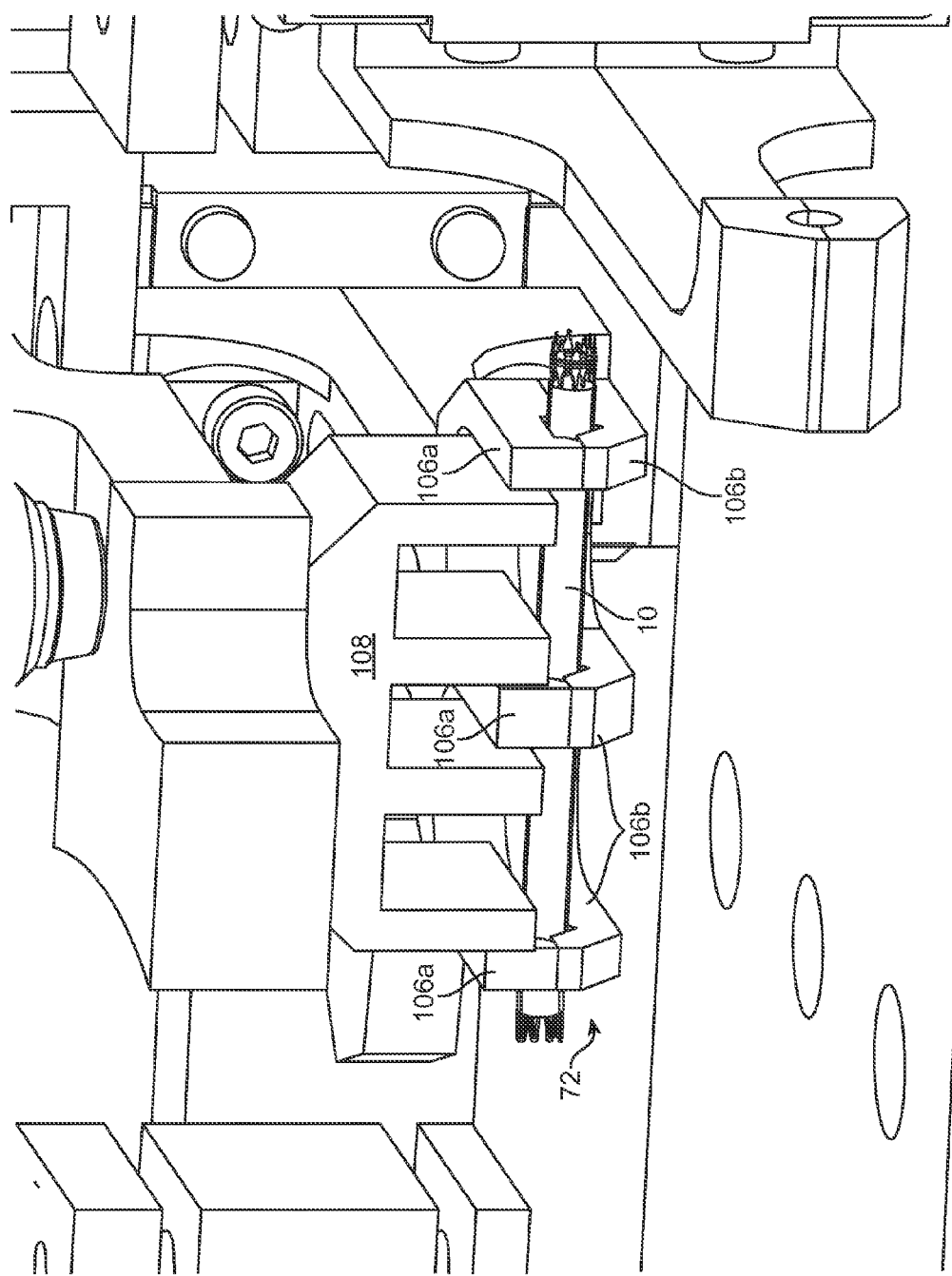
FIG. 12 is a perspective view of a stent gripper of the stent gripper assembly shown in FIGS. 7 and 11.

As shown in FIG. 12, the stent gripper 104 may have three pairs of fingers 106a, 106b, although the stent gripper may have any suitable number of finger pairs, including one, two or four pairs. In this embodiment, the three upper fingers 106a are integrally formed, and the three lower fingers 106b are also integrally formed. The fingers 106a, 106b of each pair can move away from each other to allow the stent 10 to be placed between the fingers 106a, 106b and can move towards each other to grip the stent 10 between the fingers 106a, 106b. Each pair of fingers 106a, 106b may also include grooves that are similar to or the same as the grooves 90 described above.

As shown in FIG. 12, the stent gripper 104 may also include a stripper block 108. The stripper block 108 may be used to hold the stent straight and keep it from moving during extraction and insertion of the core element 24.

As shown in FIG. 11, the apparatus 40 may also include first and second core element guides 110, 112 that are mounted on the stent gripper assembly 72, although the apparatus 40 may generally include any number of core element guides that are placed at any suitable locations. As will be described in detail below, each core element guide 110, 112 is used to guide and straighten the flexible core element 24 of the stent support 20 so that the core element 24 can be threaded through the stent 10 and the second support element 26 of the stent support 20 during stent mounting.

Figure 13:
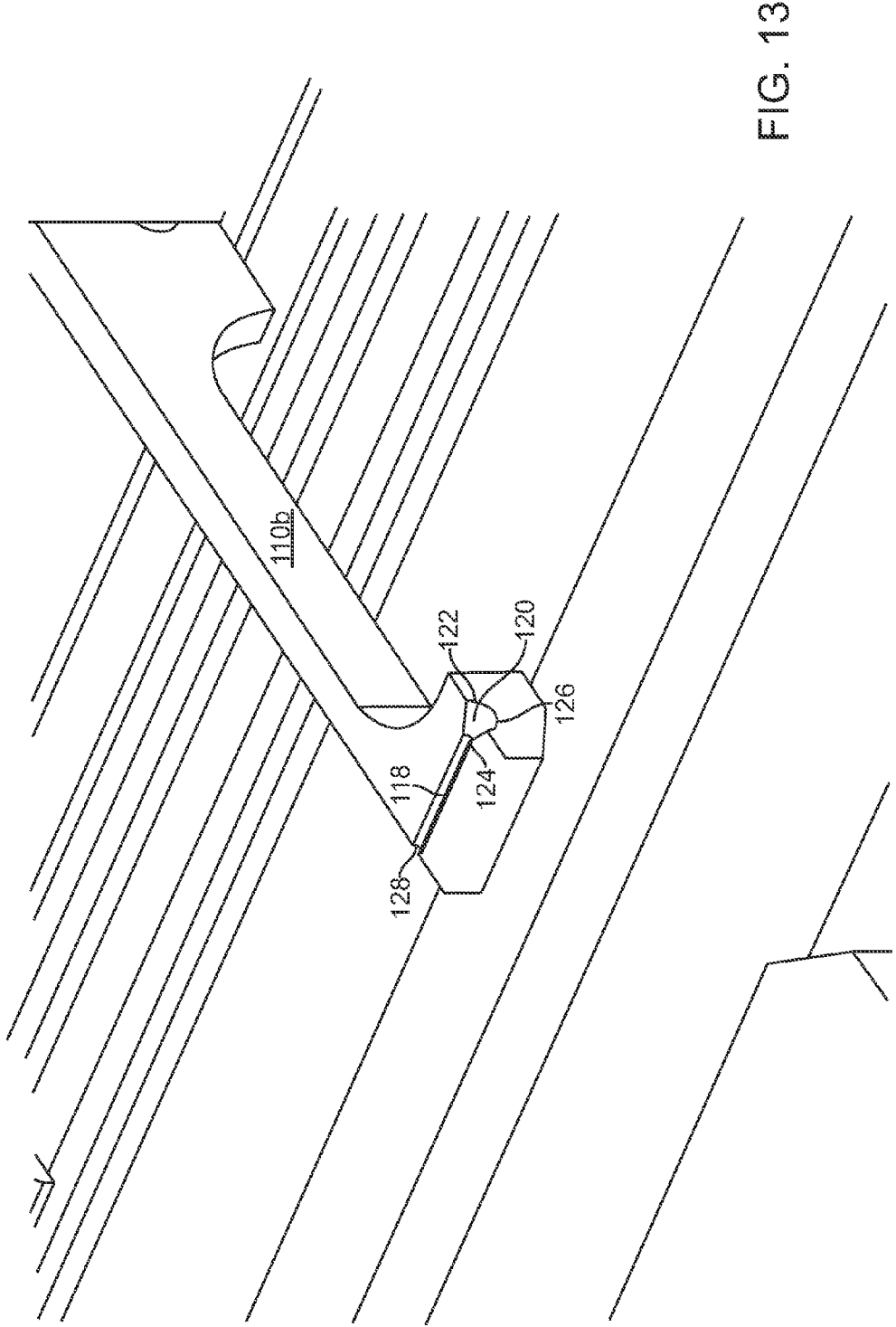
FIG. 13 is a perspective view of the lower finger of the first core element guide shown in FIGS. 7 and 11.

Preferably, each core element guide 110, 112 includes a bore 114, 116 for guiding the core element 24. The free end of the core element 24 enters from a first opening of the bore 114, 116 and exits the second opening of the bore 114, 116. The bore 114, 116 preferable has a large first opening to capture the free end of the core element 24 and a small second opening to guide and center the core element 24. As shown in FIG. 13, for example, the bore 114 of the first core element guide 110 has a cylindrical portion 118 and a conical portion 120 connected to the cylindrical portion 118. The conical portion 120 has a base 122 and an apex 124, wherein the base 74 defines the first opening 126 of the bore 114. The cylindrical portion 118 of the bore 114 defines the second opening 128 of the bore 114. During operation, as the free end of the core element 24 moves towards the first core element guide 110, the free end of the core element 24 is captured by the first opening 126 of the bore 114. As the movement of the core element 24 continues, the conical portion 120 guides the free end of the core element 24 into the small cylindrical portion 118 of the bore 114.

Figure 14:
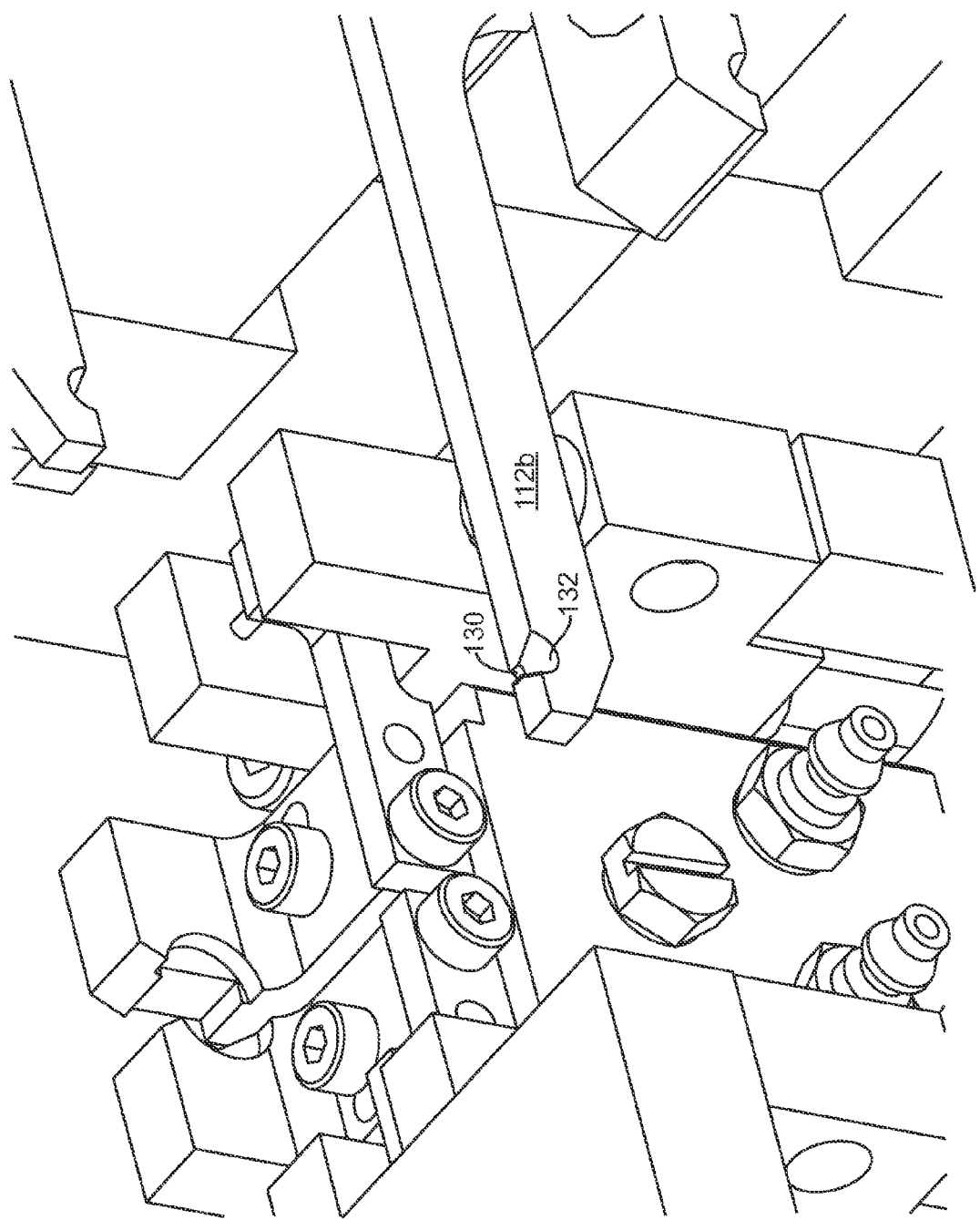
FIG. 14 is a perspective view of the lower finger of the second core element guide shown in FIGS. 7 and 11.

Similarly, as shown in FIG. 14, the bore 116 of the second core element guide 112 may also have a cylindrical portion 130 and a conical portion 132 connected with the cylindrical portion 130.

As shown in FIG. 11, the first core element guide 110 includes a pair of fingers 110a, 110b, such as an upper finger 110a and a lower finger 110b, which are moveable between an open position where the fingers 110a, 110b are apart and a closed position where the fingers 110a, 110b are next to each other. The two fingers 110a, 110b, when closed, define the bore 114 of the first core element guide 110. Preferably, the interface between the fingers 110a, 110b divides the bore 114 into an upper half and a lower half. Similarly, the second core element guide 112 may also include a pair of fingers 112a, 112b that are moveable between an open position and a closed position. The two fingers 112a, 112b, when closed, preferably define the bore 116 of the second core element guide 112. The interface between the fingers 112a, 112b preferably divides the bore 116 into an upper half and a lower half.

Each core element guide 110, 112 is moveable between two positions. The first position of each core element guide 110, 112 is the same as the first position (the middle position) of the stent gripper 104. When each core element guide 110, 112 is at its first position, its bore 114, 116 is substantially axially aligned with the stent 10 and with the first and second support elements 22, 26 of the stent support 20 to perform its function of guiding the core element 24 of the stent support 20. The second position of the each core element guide 110, 112 is a refracted position which is similar to the retracted position of the stent gripper 104.

The core element guides 110, 112 may be used in any suitable manner during stent mounting. For example, after the stent gripper 104 moves the stent 10 to the first position for stent mounting, the first and second core element guides 110, 112 may also move into their first positions to guide the core element 24 of the stent support. At this point, the stent 10 and the bores 114, 116 of the core element guides 110, 112 are substantially coaxially arranged. The first support element gripper 80 may then move the first support element 22 and core element 24 towards the stent 10 and the second support element 26. This movement causes the core element 24 to be threaded in sequence through the bore 114 of the first core element guide 110, the stent 10, the bore 116 of the second core element guide 112, and the second support element 26.

As the first support element gripper 80 moves the first support element 22 and core element 24 towards the second support element 26, the second support element gripper 82 may also move the second support element 26 toward the first support element 22 and core element 24. After the stent 10 and second support element 26 have been mounted on the core element 24, the fingers 110a, 110b, 112a, 112b of each core element guide 110, 112 are opened to disengage the core element guides 110, 112 from the core element 24 of the stent support 20.

As shown in FIG. 5, the apparatus 40 may include two scale assemblies 48 for weighing a stent 10, although it may include any number of scale assemblies, such as one, three, or four scale assemblies. In the illustrated embodiment, the scale assemblies 48 and the stent gripper assembly 72 are placed on the opposite sides of the stent support gripper assembly 70, although they can be placed on the same side. To place a stent 10 in one of the scale assemblies 48, the stent gripper assembly 72 and the stent support gripper assembly 70 can be positioned longitudinally so that they are aligned with this scale assembly 48.

Figure 15:
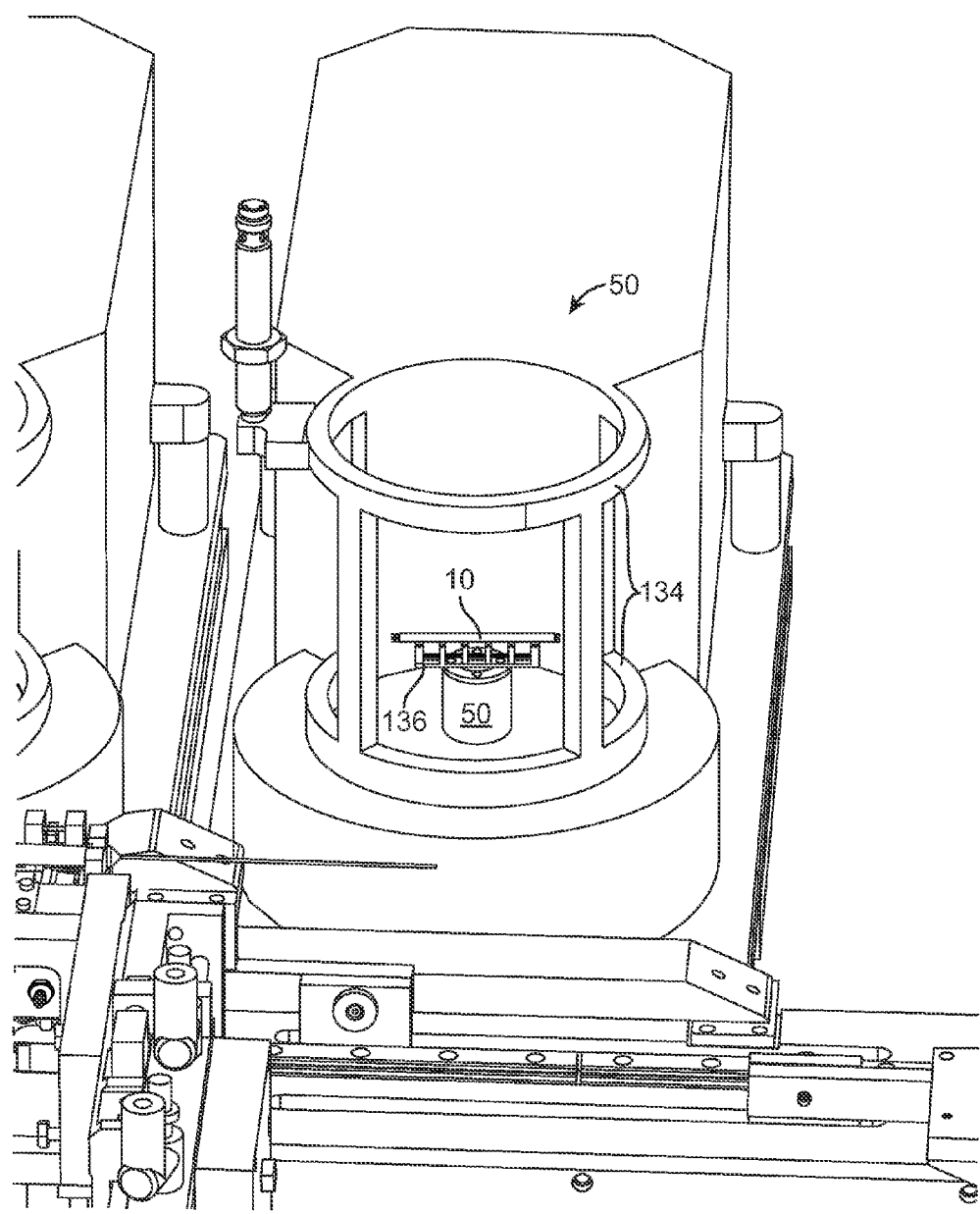
FIG. 15 is a perspective view of a scale assembly of the apparatus shown in FIG. 5.

As shown in FIG. 15, each scale assembly 48 includes a housing 134, a scale 50 disposed in the housing 134, and a stent nest 136 resting on the scale 50. In the illustrated embodiment, the housing 134 preferably has a door (not shown) that opens to allow the stent gripper 104 to place a stent 10 on the scale 50 or to remove a stent 10 from the scale 50. The door can be closed to isolate the scale 50 from the effects of air disturbance and noise. Air disturbance and noise may affect the accuracy of the scale 50 due to the scale's sensitivity.

The scale 50 may be any scale suitable for measuring stent weight, such as a scale that is commercially available. For example, the scale 50 may be a microbalance, such as the UMX5 Microbalance from Mettler-Toledo, Inc. of Columbus, Ohio. The maximum capacity of the UMX5 Microbalance including a weighing pan is 2.1 g. The weight of a coated stent that this scale can measure may be approximately 0.4 g.

As shown in FIG. 16, the stent nest 136 has a horizontal member 138 and a plurality of vertical members 140 that extend upwards from the horizontal member 138. The horizontal member 138 of the stent nest 136 rests on the scale 50, and the stent 10 rests on top of the vertical members 140. The top surface 142 of each vertical member 140 may include a notch 144, in which the stent 10 may rest. In order for the stent gripper 104 to place a stent 10 into the notches 144 of the vertical members 140, each of its lower fingers 106b may need to extend into the space 146 between two adjacent vertical members 140 of the stent nest 136. Therefore, the space 146 between two adjacent vertical members 140 preferably is sufficiently wide and sufficiently high to accommodate a lower finger 106b of the stent gripper 104.

After the stent 10 has been placed on the stent nest 136, the scale 50 begins to measure stent weight. The weight signal measured by the scale 50 generally includes a constant stent weight and disturbances that vary with time. Because the stent weight is small, the disturbances may sometimes constitute a significant portion of the measured signal. To minimize the effects of disturbances, the scale 50 does not measure stent weight until the disturbances (oscillations) in the measured signal is below a certain value for a given period of time.

Preferably, the stent nest 136 is not attached or joined to the scale 50. Instead, the stent nest 136 merely rests on top of the scale 50 under the gravity of the stent nest 136. This may be desirable because if the stent gripper 104 collides with the stent nest 136, it would not damage the scale 50; it would just knock the stent nest 136 off the scale 50.

As shown in FIG. 5, the apparatus 40 for weighing a stent may further include a plurality of mounts 148 that reduce the amount of ground vibration transmitted to the scales 50. The inventors discovered that a substantial portion of disturbances experienced by the scales 50 is transmitted to the scales 50 from the ground and that the ground vibration generally has predictable frequency content. The inventors further discovered that the amount of ground vibration transmitted to the scales 50 can be significantly reduced by carefully selecting the elasticity and damping characteristics of the mount material in consideration of the mass of the apparatus 40. Preferably, ground vibration is first measured and its frequency content is determined. Then the system natural frequency, which is mostly a function of the mass of the apparatus 40 and the elasticity of the mounts 148, is selected so that the system natural frequency is less than most of the frequency components of ground vibration. The system natural frequency may be less than 60% of the frequency components of ground vibration, preferably less than 80%, more preferably less than 90%, most preferably less than 95%. Such a system natural frequency can significantly reduce the amount of ground vibration transmitted to the scales 50. The system damping ratio, which is a function of the mass of the apparatus 40 and the elasticity and damping characteristics of the mounts 148, is preferably about 0.1 to 2.0, more preferably about 0.4 to 1.2, most preferably about 0.6 to 1.0.

The above-described stent-weighing apparatus 40 can be operated in several ways. According to one way of operating the stent-weighing apparatus 40, the first step is to use the robotic arm 44 to move a stent 10 to be weighed from the buffer 42 to the stent support gripper assembly 70. The robotic arm 44 is placed in its first position next to the buffer 42 to pick up the stent 10 to be weighed. At this point, the robotic arm 44 is at the lower vertical position. The robotic arm 44 grips the stent support 20 on which the stent 10 is mounted, with the stent support griper 56 of the robotic arm 44 gripping the first support element 22 of the stent support 20 and the core element holder 58 holding the core element 24 of the stent support 20. At this point, the stent support 20 is still in a receptacle 54 of the buffer 42. Then the robotic arm 44 is raised to its higher vertical position, as shown in FIG. 6, to lift the stent support 20 out of the receptacle 54. Next the first member 64 of the robotic arm 44 is rotated 180° relative to the second member 66 to move the stent support 20 from the vertical position as shown in FIG. 6 to a horizontal position just above the stent support gripper assembly 70.

In the next step, the stent support gripper assembly 70 receives the stent support 20 from the robotic arm 44 and removes the stent 10 from the stent support 20. To receive the stent support 20 from the robotic arm 44, the first and second support element grippers 80, 82 of the stent support gripper assembly 70 are positioned below the first and second support elements 22, 26 of the stent support 20, respectively. And the fingers 86, 92 of the first and second support element grippers 80, 82 are positioned apart to receive the first and second support elements 22, 26 of the stent support 20, respectively. The robotic arm 44 is then lowered from its higher vertical position to its lower vertical position to place the first and second support elements 22, 26 of the stent support 20 between the fingers 86, 92 of the first and second support element grippers 80, 82, respectively. At this point, the fingers 86 of the first support element gripper 80 are preferably aligned with the groove 30 of the first support element 22, and the fingers 92 of the second support element gripper 82 are aligned with the groove 34 of the second support element 26. Next the fingers 86 of the first support element gripper 80 move towards each other to grip the first support element 22 at its groove 30, and the fingers 92 of the second support element gripper 82 also move towards each other to grip the second support element 26 at its groove 34. The stent support gripper assembly 70 then moves longitudinally to align the stent 10 with the stent gripper 104 of the stent gripper assembly 72 so that the stent gripper 104 can grip the stent 10 for dismounting.

At this time, the stent gripper 104 of the stent gripper assembly 72 preferably is aligned with the scale 50 that is to be used to weigh the stent 10. Once the stent 10 is aligned with the stent gripper 104, the stent gripper 104 moves from its second position (the refracted position) to its first position (the middle position) with its fingers 106a, 106b open to grip the stent 10. After reaching its first position, the stent gripper 104 closes its fingers 106a, 106b to grip the stent 10. Then the first and second support element grippers 80, 82 of the stent support gripper assembly 70 move away from each other in the longitudinal direction 76. This movement removes the second support element 26 of the stent support 20 from the core element 24 of the stent support 20. The movement also extracts the core element 24 of the stent support 20 from the hollow center of the stent 10. As a result, the stent 10 is removed from the stent support 20.

At this point, the stent gripper 104 may extend further to its third position to place the stent 10 on the scale 50. Alternatively, the stent gripper 104 may move back to the retracted position. And the stent support gripper assembly 70 may mount the second support element 26 of the stent support 20 on the core element 24 of the stent support 20, and move the stent support 20 to one side of the stent gripper 104 before the stent gripper 104 extends from the retracted position to its third position to place the stent 10 on the scale 50. Mounting the second support element 26 on the core element 24 may require that the first and second core element guides 110, 112 move into their first positions to guide the core element 24 before the first and second support element grippers 80, 82 move the first and second support elements 22, 26 of the stent support 20 towards each other to mount the second support element 26 on the core element 24.

To place the stent 10 on the stent nest 136 on top of the scale 50, the stent gripper 104 extends its lower fingers 106b into the respective spaces 146 between two adjacent vertical members 140 of the stent nest 136 to place the stent 10 into the notches 144 of the vertical members 140. The upper and lower fingers 106a, 106b of the stent gripper 104 then move apart to release the stent 10.

After the stent 10 has been placed on the stent nest 136, the door of the scale assembly's housing 134 is closed, and the scale 50 begins to measure stent weight. The signal measured by the scale 50 generally includes a constant stent weight and disturbances that vary with time. Because the stent weight is small, the disturbances may sometimes constitute a significant portion of the measured signal. To minimize the effects of disturbances, the scale 50 does not measure stent weight until the disturbances (oscillations) in the measured signal is below a certain value for a given period of time.

After a reading of the stent weight has been obtained, the stent 10 is removed from the scale 50 and is again mounted on the stent support 20. The procedure for mounting the stent 10 on the stent support 20 may vary depending on whether, as described previously, the second support element 26 has been mounted on the core element 24 and moved to one side of the stent gripper 104. If this is the case, the stent gripper 104 may move the stent 10 from the scale 50 to the retracted position so that the stent support gripper assembly 70 can remove the second support element 26 from the core element 24 and place the second support element 26 and the core element 24 on different sides of the stent gripper 104. Then the stent gripper 104 can move the stent 10 from the retracted position to the middle position so that the stent 10 can be mounted on the stent support 20. If this is not the case (i.e., the second support element 26 and the core element 24 are already on different sides of the stent gripper 104), the stent gripper 104 may move the stent 10 from the scale 50 directly to the middle position so that the stent 10 can be mounted on the stent support 20.

After the stent gripper 104 has moved the stent 10 to the first (middle) position, the first and second core element guides 110, 112 also move into their first positions to guide the core element 24 of the stent support so that the core element 24 can be threaded through the stent 10 and the second support element 26. At this point, the stent 10 and the bores 114, 116 of the core element guides 110, 112 are substantially coaxially arranged. The first support element gripper 80 may then move the first support element 22 and core element 24 towards the stent 10 and the second support element 26. This movement causes the core element 24 to be threaded in sequence through the bore 114 of the first core element guide 110, the stent 10, the bore 116 of the second core element guide 112, and the second support element 26. As the first support element gripper 80 moves the first support element 22 towards the second support element 26, the second support element gripper 82 may also move the second support element 26 toward the first support element 22. After the stent 10 and second support element 26 have been mounted on the core element 24, the fingers 110a, 110b, 112a, 112b of the core element guides 110, 112 are opened to disengage the core element guides 110, 112 from the core element 24 of the stent support 20.

After the stent 10 has been mounted on the stent support 20, the robotic arm 44 may move the stent support 20 from the stent support gripper assembly 70 to the buffer 42. To this end, the robotic arm 44 is placed in its position to pick up the stent support 20 from the stent support gripper assembly 70. The stent support gripper assembly 70 preferably moves the stent support 20 in a position where the first support element 22 of the stent support 20 is aligned with the stent support griper 56 of the robotic arm 44 and the core element 24 of the stent support 20 is aligned the core element holder 58 of the robotic arm 44. Next the fingers 86 of the first support element gripper 80 move away from each other to release the first support element 22, and the fingers 92 of the second support element gripper 82 also move away from each other to release the second support element 26. Then the robotic arm 44 is lowered to grip the stent support 20, with the stent support griper 56 of the robotic arm 44 gripping the first support element 22 of the stent support 20 and the core element holder 58 holding the core element 24 of the stent support 20. Next the robotic arm 44 is raised to lift the stent support 20 from the stent support gripper assembly 70. The first member 64 of the robotic arm 44 is rotated 180° relative to the second member 66 to move the stent support 20 from this horizontal position to the vertical position as shown in FIG. 6. Then the robotic arm 44 is lowered to place the stent support 20 in a receptacle 54 of the buffer 42.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A robotic arm for moving a stent support, comprising:
   a first member;
   a second member supporting the first member, the first member configured to move from a first position to a second position by rotating 180 degrees relative to the second member;
   a gripper configured to grip a first part of the stent support; and
   a holder configured to grip a second part of the stent support,
   wherein the gripper and holder are disposed on a first member, are configured to hold the stent support in a vertical position when the first member is in the first position, and are configured to hold the stent support in a horizontal position when the first member is in the second position.

2. The robotic arm of claim 1, wherein the gripper includes movable fingers configured to grip the first part of the stent support.

3. The robotic arm of claim 2, wherein the holder includes a groove configured to hold the second part of the stent support.

4. The robotic arm of claim 1, wherein an interface between the first member and the second member is oriented at 45° from the vertical position.

5. The robotic arm of claim 1, wherein when the first member is in the first position relative to the second member, the gripper and the holder are configured to move vertically upward.

6. The robotic arm of claim 1, wherein when the first member is in the second position relative to the second member, the gripper and the holder are configured to move vertically downward.

7. A stent support gripper assembly comprising:
   a rail;
   a first support element gripper for gripping a first support element of a stent support, the first support element gripper connected to the rail and configured to move along the rail while gripping the first support element; and
   a second support element gripper for gripping a second support element of the stent support, the second support element gripper connected to the rail and configured to move along the rail while gripping the second support element,
   wherein the first support element gripper and the second support element gripper, while both are connected to the rail, are configured to move toward each other along the rail and to move away from each other along the rail.

8. The assembly of claim 7, wherein the first support element gripper includes fingers configured to move toward each other to grip the first support element of the stent support.

9. The assembly of claim 8, wherein the fingers of the first support element gripper are configured to move laterally toward each other.

10. The assembly of claim 7, wherein the second support element gripper includes fingers configured to move toward each other to grip the second support element of the stent support.

11. The assembly of claim 10, wherein the second support element gripper includes a core element holder for holding a core element of the stent support.

12. The assembly of claim 10, wherein the fingers of the second support element gripper are configured to move laterally toward each other.

13. The assembly of claim 7, wherein the first support element gripper and the second support element gripper are mounted on a platform and are moveable independently of each other on the platform, and the platform is movable along the rail.

14. The assembly of claim 7, further comprising a platform movable along the rail and in a longitudinal direction, wherein the first support element gripper and the second support element gripper are configured to move in the longitudinal direction with the platform.

* * * * *